US009298418B2

(12) United States Patent
Crowley

(10) Patent No.: US 9,298,418 B2
(45) Date of Patent: Mar. 29, 2016

(54) ELECTRONIC ANALYSIS OF ATHLETIC PERFORMANCE

(71) Applicant: InfoMotion Sports Technologies, Inc., Attleboro, MA (US)

(72) Inventor: Michael James Crowley, Attleboro, MA (US)

(73) Assignee: InfoMotion Sports Technologies, Inc., Attleboro, MA (US)

( * ) Notice: Subject to any disclaimer, the term of this patent is extended or adjusted under 35 U.S.C. 154(b) by 0 days.

(21) Appl. No.: 14/046,180

(22) Filed: Oct. 4, 2013

(65) Prior Publication Data

US 2014/0039651 A1 Feb. 6, 2014

Related U.S. Application Data

(63) Continuation of application No. 12/369,680, filed on Feb. 11, 2009, now Pat. No. 8,579,632.

(60) Provisional application No. 61/028,823, filed on Feb. 14, 2008.

(51) Int. Cl.
*G06F 7/00* (2006.01)
*A63B 69/00* (2006.01)
*G06Q 30/02* (2012.01)
*G09B 19/00* (2006.01)

(52) U.S. Cl.
CPC .............. *G06F 7/00* (2013.01); *A63B 69/0071* (2013.01); *G06Q 30/02* (2013.01); *G09B 19/0038* (2013.01)

(58) Field of Classification Search
CPC ........................ G09B 19/0038; A63B 2225/50

USPC .................................. 434/247, 252, 251, 249
See application file for complete search history.

(56) References Cited

U.S. PATENT DOCUMENTS

| 3,229,976 A | 1/1966 | Walter |
| 4,479,649 A | 10/1984 | Newcomb et al. |
| 4,577,865 A | 3/1986 | Shishido |

(Continued)

FOREIGN PATENT DOCUMENTS

| CN | 1524004 | 8/2004 |
| CN | 1814333 | 8/2006 |

(Continued)

OTHER PUBLICATIONS

U.S. Appl. No. 61/028,823, filed Feb. 14, 2008, Crowley.

(Continued)

*Primary Examiner* — Peter Egloff
(74) *Attorney, Agent, or Firm* — Fish & Richardson P.C.

(57) ABSTRACT

The subject matter of this specification can be embodied in, among other things, a computer-implemented athletic performance analysis method that includes obtaining, at a computer system, first motion data reflecting motion of a sporting device during one or more drills performed by an athlete. The method also includes creating and storing action data by identifying a plurality of portions of the motion data, where each of the portions correspond to one or more actions by the athlete; comparing the action data for the athlete, with the computer system, to corresponding aggregated action data for a plurality of other athletes to determine a relative skill level for the athlete with respect to the one or more actions; and generating data for a report that reflects the relative development level of the athlete.

24 Claims, 12 Drawing Sheets

(56) References Cited

U.S. PATENT DOCUMENTS

| | | | |
|---|---|---|---|
| 4,595,200 A | 6/1986 | Shishido | |
| 4,776,589 A | 10/1988 | Yang | |
| 5,102,131 A | 4/1992 | Remington | |
| 5,236,383 A | 8/1993 | Connelly | |
| 5,609,411 A | 3/1997 | Wang | |
| 5,779,576 A | 7/1998 | Smith et al. | |
| 5,810,685 A | 9/1998 | Willner et al. | |
| 5,888,156 A | 3/1999 | Cmiel et al. | |
| 6,013,007 A | 1/2000 | Root et al. | |
| 6,148,271 A | 11/2000 | Marinelli | |
| 6,196,932 B1 | 3/2001 | Marsh et al. | |
| 6,251,035 B1 | 6/2001 | Fa | |
| 6,565,449 B2 | 5/2003 | Buhler | |
| 6,582,330 B1 | 6/2003 | Rehkemper et al. | |
| 6,671,390 B1 | 12/2003 | Barbour et al. | |
| 6,744,375 B1 | 6/2004 | Groos | |
| 6,757,572 B1 | 6/2004 | Forest | |
| 6,856,934 B2 | 2/2005 | Vock et al. | |
| 7,014,581 B2 | 3/2006 | Ng | |
| 7,021,140 B2 | 4/2006 | Perkins | |
| 7,072,789 B2 | 7/2006 | Vock et al. | |
| 7,092,846 B2 | 8/2006 | Vock et al. | |
| 7,162,392 B2 | 1/2007 | Vock et al. | |
| 7,192,387 B2 | 3/2007 | Mendel | |
| 7,234,351 B2 | 6/2007 | Perkins | |
| 7,273,431 B2 | 9/2007 | DeVall | |
| 7,308,818 B2 | 12/2007 | Considine et al. | |
| 7,625,314 B2 * | 12/2009 | Ungari et al. | 482/1 |
| 7,643,895 B2 | 1/2010 | Gupta et al. | |
| 7,813,821 B1 | 10/2010 | Howell | |
| 7,891,666 B2 | 2/2011 | Kuenzler et al. | |
| 8,070,654 B2 | 12/2011 | Chapa, Jr. et al. | |
| 8,078,478 B2 | 12/2011 | Fleming et al. | |
| 8,083,646 B2 | 12/2011 | Chapa, Jr. et al. | |
| 8,086,421 B2 | 12/2011 | Case, Jr. et al. | |
| 8,109,858 B2 | 2/2012 | Redmann | |
| 8,112,251 B2 | 2/2012 | Case, Jr. et al. | |
| 8,128,410 B2 | 3/2012 | Prstojevich | |
| 8,152,695 B2 | 4/2012 | Riley et al. | |
| 8,172,722 B2 | 5/2012 | Molyneux et al. | |
| 8,206,219 B2 | 6/2012 | Shum et al. | |
| 8,231,487 B2 | 7/2012 | Nurnberg et al. | |
| 8,231,506 B2 | 7/2012 | Molyneux et al. | |
| 8,517,870 B2 | 8/2013 | Crowley et al. | |
| 8,540,560 B2 | 9/2013 | Crowley et al. | |
| 8,579,632 B2 | 11/2013 | Crowley | |
| 8,597,095 B2 | 12/2013 | Crowley et al. | |
| 8,663,040 B2 | 3/2014 | Kortegast | |
| 8,951,106 B2 | 2/2015 | Crowley et al. | |
| 2003/0207718 A1 | 11/2003 | Perlmutter | |
| 2003/0224885 A1 | 12/2003 | Leal et al. | |
| 2003/0228934 A1 | 12/2003 | Corzilius et al. | |
| 2005/0069853 A1 | 3/2005 | Tyson et al. | |
| 2005/0288133 A1 | 12/2005 | Rudell | |
| 2006/0025282 A1 | 2/2006 | Redmann | |
| 2006/0135297 A1 | 6/2006 | Cruciani | |
| 2006/0148594 A1 | 7/2006 | Saintoyant et al. | |
| 2006/0189386 A1 | 8/2006 | Rosenberg | |
| 2007/0021244 A1 | 1/2007 | Ko | |
| 2007/0026975 A1 * | 2/2007 | Marty et al. | 473/467 |
| 2007/0281811 A1 | 12/2007 | Wang | |
| 2008/0015064 A1 | 1/2008 | Nelson et al. | |
| 2008/0026877 A1 | 1/2008 | Neel | |
| 2008/0139307 A1 | 6/2008 | Ueshima et al. | |
| 2008/0300905 A1 * | 12/2008 | Kelley, III | 705/1 |
| 2009/0029754 A1 | 1/2009 | Slocum et al. | |
| 2009/0047645 A1 | 2/2009 | Dibenedetto et al. | |
| 2009/0048044 A1 | 2/2009 | Oleson et al. | |
| 2009/0048070 A1 | 2/2009 | Vincent et al. | |
| 2009/0112692 A1 * | 4/2009 | Steelberg et al. | 705/10 |
| 2009/0189982 A1 | 7/2009 | Tawiah | |
| 2009/0210078 A1 | 8/2009 | Crowley | |
| 2009/0298650 A1 | 12/2009 | Kutliroff | |
| 2009/0325739 A1 | 12/2009 | Gold | |
| 2010/0048302 A1 | 2/2010 | Lutnick et al. | |
| 2010/0053324 A1 | 3/2010 | Kim et al. | |
| 2010/0069181 A1 | 3/2010 | Lin | |
| 2010/0105480 A1 | 4/2010 | Mikhailov et al. | |
| 2010/0130315 A1 | 5/2010 | Steidle | |
| 2010/0184563 A1 | 7/2010 | Molyneux et al. | |
| 2010/0285903 A1 | 11/2010 | Nicodem | |
| 2011/0077112 A1 | 3/2011 | Erario et al. | |
| 2011/0118062 A1 | 5/2011 | Krysiak et al. | |
| 2011/0220634 A1 | 9/2011 | Yeh | |
| 2011/0316529 A1 | 12/2011 | Stancil et al. | |
| 2012/0029666 A1 | 2/2012 | Crowley | |
| 2012/0058845 A1 | 3/2012 | Crowley | |
| 2012/0129138 A1 | 5/2012 | Redmann | |
| 2012/0231906 A1 | 9/2012 | Barry et al. | |
| 2013/0079906 A1 | 3/2013 | Crowley et al. | |
| 2014/0031151 A1 | 1/2014 | Crowley | |
| 2014/0081436 A1 | 3/2014 | Crowley et al. | |

FOREIGN PATENT DOCUMENTS

| | | |
|---|---|---|
| CN | 101367013 | 2/2009 |
| EP | 1 637 192 | 3/2006 |
| JP | 2007-014671 | 1/2007 |
| KR | 10-1988-0001317 | 4/1988 |
| KR | 2000055834 | 9/2000 |
| KR | 2001008367 | 2/2001 |
| WO | WO 95/34351 | 12/1995 |
| WO | WO 99/16511 | 4/1999 |
| WO | WO 2010/111705 | 9/2010 |
| WO | WO 2012/033732 | 3/2012 |

OTHER PUBLICATIONS

U.S. Appl. No. 61/164,277, filed Mar. 27, 2009, Crowley.

U.S. Appl. No. 61/249,526, filed Oct. 7, 2009, Crowley.

"Built-in Speed Sensor Records How Fast You Throw the Ball—Used As a Training Aid for Pitchers," Markwort Sporting Goods Company [online], [retrieved on May 22, 2012] Retrieved from the Internet:<URL: http://www.markwort.com/featured/speedsensor.asp>.

"Intelligent Basketball Tracks Trajectory," Freescale [online] [retrieved on May 23, 2012]. Retrieved from the Internet: <URL: http:/www.freescale.com/webapp/sps/site/overview.jsp?code=CASE_STUDY_INTELLIGENT_BASKETBALL>, 2 pages.

"Speed Sensor™ Programmable Balls," Markwort [online], [retrieved on May 25, 2012]. Retrieved from the Internet: <URL: http://www.markwort.com/featured_tab/speedsensor_big.asp>, 2 pages.

Murray, "Freescale Rolls Out World's First Intelligent Basketball," Design News Blog, Jun. 29, 2007 [retrieved May 22, 2012] Retrieved from the Internet:<URL: http://www.designnews.com/author.asp?section_id=1386&doc_id=215078&print=yes>.

Hsu, Michael. "Gear & Gadgets: Making Sense of Your Swing, Turn Your Golf Glove Into a High-Tech Coach." The Wall Street Journal, Aug. 4-5, 2012. (1 page).

Authorized Officer D. Kim, International Search Report and Written Opinion for PCT/US2010/029068, mailed Oct. 21, 2010, 13 pages.

Authorized Officer RA Kwang Pyo, International Search Report/Written Opinion in PCT/US2009/033831 mailed Sep. 24, 2009, 11 pages.

Authorized Officer S. Baharlou, International Preliminary Report on Patentability for PCT/US2010/029068, mailed Oct. 6, 2011, 9 pages.

Authorized Officer Y. Cussac, International Preliminary Report on Patentability in PCT/US2009/033831, mailed Aug. 26, 2010, 6 pages.

International Search Report and Written Opinion in International Application No. PCT/US2011/050498, mailed Apr. 25, 2012, 9 pages.

International Preliminary Report on Patentability in International Application No. PCT/US2011/050498, mailed Mar. 12, 2013, 6 pages.

(56) References Cited

OTHER PUBLICATIONS

International Search Report and Written Opinion in International Application No. PCT/US2013/048958, mailed Sep. 27, 2013, 15 pages.
International Search Report and Written Opinion in International Application No. PCT/US2013/048649, mailed Oct. 22, 2013, 10 pages.
International Preliminary Report on Patentability in International Application No. PCT/US2013/048649, issued Jan. 6, 2015, 7 pages.
International Preliminary Report on Patentability in International Application No. PCT/US2013/048958, mailed Jan. 15, 2015, 12 pages.
Extended European Search Report in EP Application No. 11824001.9, dated Apr. 3, 2014, 6 pages.

\* cited by examiner

InfoMotion Sports Technologies
Skill Diagnostic Report

Name: 
Height: 65 Inches  Age: 14
Weight: 115 lbs  Grade: 10
Test Date: Sep-09  Test Location: Mass Premier Courts

Skill Diagnostics

| | Total Dribbles | Avg. Dribble Height (cm) | Avg. Force | Errors | Min/Max Range (cm) | Test Score |
|---|---|---|---|---|---|---|
| Stationary Ballhandling | | | | | | |
| Stationary Figure 8 | 75 | 55 | 32 | 2 | 15 | 65 |
| Stationary Behind Back | 45 | 34 | 30 | 1 | 12 | 60 |
| Stationary Two Ball RH | 60 | 21 | 35 | 3 | 9 | 45 |
| Stationary Two Ball LH | 78 | 25 | 28 | 3 | 13 | 60 |
| Camp Rank | 85 | 75 | 65 | 80 | 34 | 60 |
| Athletic Ballhandling | | | | | | |
| Athletic Shuttle with Dribble | 46 | 54 | 45 | 1 | 12 | |
| Athletic Half Court with Dribble | 35 | 58 | 50 | 0 | 15 | |
| Athletic Weave - Half Court | 40 | 45 | 52 | 1 | 17 | |

| | Attempted | Made | % | Avg. Release (ms) | Release Ratio |
|---|---|---|---|---|---|
| Shooting | | | | | |
| 3 Point 20 Shot Release Time | 20 | 8 | 40.00% | 0.03 | 13.333 |

| | Jump 1 | Jump 2 | Avg. | | |
|---|---|---|---|---|---|
| Athletic Skills | | | | | |
| Vertical Jump - 1 Step with Ball | 28 | 27 | 27.5 | | |

| Skill Predictor | Score | 55.1 | Level | HS Varsity |
|---|---|---|---|---|
| Predictor Confidence | | 85% | | |

Skill Development History

Predictor Scores
| Test Date | Aug-08 | Feb-09 | Jul-09 | Current |
|---|---|---|---|---|
| Total Predictor Score | 34 | 38 | 42 | 55.1 |
| % Improvement - Previous Test | 0.00% | 11.76% | 10.53% | 31.19% |

Drill Specific Scores
| | Aug-08 | Feb-09 | Jul-09 | Current |
|---|---|---|---|---|
| Figure 8 | 40 | 45 | 49 | 65 |
| Behind Back | 72 | 75 | 80 | 80 |
| 3 Point Shooting | 10.5 | 11.4 | 12 | 13.333 |
| Two Ball RH | 33 | 38 | 42 | 45 |

Diagnostic Analysis

| | Time in Hand | Force | Stand Dev | Avg Height |
|---|---|---|---|---|
| Strong Hand Vs Weak Hand | 0.45 | 32 | 2.5 | 3.5 |

FIG. 5A

ELECTRONIC ANALYSIS OF ATHLETIC PERFORMANCE

CROSS-REFERENCE TO RELATED APPLICATIONS

This application claims the benefit of U.S. provisional application 61/028,823 filed Feb. 14, 2008. The disclosure of the prior application is considered part of (and is incorporated by reference in) the disclosure of this application.

TECHNICAL FIELD

This document relates to systems and techniques for monitoring and comparing certain aspects of athletic performance by a first athlete against other athletes.

BACKGROUND

Athletics has become an integral part of society, with multiple television channels dedicated to sporting events, with professional athletes promoting all sorts of products, and with the public holding star athletes—both amateur and professional—in high regards, so as to support financial rewards such as college scholarships, sponsorship opportunities, and other revenue-generating careers. With greater general attention on athletics comes greater attention on improving athletic performance. Today's athletes, beginning as early as the elementary school level, specialize in particular areas and train year-round to improve their skills and their conditioning. With athletics leading to a possibly lucrative career for some, and to academic assistance in the form of scholarships to others, more and more athletes have looked to improve their performance in various manners.

Good coaching and personal dedication are some of the best known ways to improve an athlete's performance. A talented coach can often observe subtle problems in an athlete's style of play, and can direct the player to correct those problems. Likewise, a talented trainer can direct an athlete to follow certain regimens to improve physiological weaknesses.

Despite the talent and experience obtained by many top coaches or athletic experts, human perception can capture and fully appreciate only a small subset of the factors that affect an athlete's performance. Thus, despite years of observing how different athletes compete in a given sport or having competed for many years themselves, the most highly skilled trainers and coaches still do not have the ability to quantify very small differences in motion of what they see. These differences in motion can be the most important elements in comparing and diagnosing a player's skill. Also, techniques that rely on human observation and judgment are prone to a high degree of opinion or bias based on the perceptions of any single observer. This bias, and the wide variability of what any given observer believes they are seeing, negatively affects the advice that coaches and trainers can provide to athletes, and also negatively affects the athletes' perception of the advice they are being given (i.e., an athlete may ignore good advice if they think that the provider of the advice does not appreciate their abilities).

In some sports that require a combination of physical athletic skill, muscle memory, and hand-eye coordination skills to be used while simultaneously moving an athletic object, such as a ball, while under pressure situations, the ability to objectively quantify and compare discrete skill differences between players is almost impossible using human perception. The net effect of the inability to standardize the unseen elements of skill has been an over-reliance on only the measurable physical aspects of certain sports, such as athletic speed, strength, and jumping, which causes many highly skilled athletes to be overlooked.

SUMMARY

This document describes systems and techniques that may be used to quantify and benchmark an athlete's current skill proficiency using sensors that capture discrete movements of an athletic device, such as a basketball or soccer ball, while it is in motion so as to link athletic proficiency of the athlete to their ability to control the athletic device, compare the related performance of the athlete controlling the movement of the athletic device to the performance of other athletes that has been aggregated to provide base performance indicators, and to provide feedback for an athlete so that they can improve their performance.

Motion-related data from the athletic device, such as acceleration and rotation data, can be identified and compiled into meaningful samples, and the samples can be compared to a large number of other samples collected in a similar fashion from athletes having known skill levels. For example, the characteristics of athletic performance for a certain action or athletic drill performed while using the athletic device can be determined for each level of play, e.g., grade school, high school, lower level college (e.g., division II or junior college), higher level college, professional, and elite or all star. Sampled data for a particular athlete can then be compared to aggregated data, collected using the same motion sensing technologies and while performing the same drills in the same fashion, from other athletes that were known to be performing at each of these levels, and a level of performance for the particular athlete may thus be determined.

The drills can be predetermined and matched between and among test subjects so that the resulting data can be matched and compared as between individuals in a statistically significant manner. Drills are defined multi-step physical processes that an athlete performs, such as dribbling in a particular pattern, shooting a certain number of shots from a defined point on a court, and running through a pattern, such as through cones or on a line that can be applied to a floor.

As a result, such techniques can provide an indication to an athlete or to recruiting personnel regarding the objective skill level at which the athlete is performing, either for a particular skill set, or overall for an entire sport. In addition, the results may provide constructive feedback by suggesting exercises that the athlete can undertake to improve any deficiencies that the system recognized when comparing the athlete's data to that of other athletes.

In certain implementations, such systems and techniques may provide one or more advantages. For example, athletes can be analyzed quickly by being run through a number of drills that are instantly recorded and easily transferred to a computing system. Also, the systems can record facets of an athlete's performance that would not be observable by a coach watching the athlete, particularly for fast-moving sports that require a combination of athleticism, muscle memory, vision, and the like to succeed. In addition, the analysis provided by the techniques provided herein can be consistent and unbiased so as to provide high quality, objective analysis in a highly scalable system without the need for personal training of numerous observers. For example, motion sensing testing systems can be deployed nationally for operation by technicians who have only limited amounts of training. The analysis, like the data collection, can be unbiased and scalable, so that it can give an athlete a fair evaluation without concern that assertions of favoritism will be made, and can be completed without needing to train numerous analysts as a system grows.

In one implementation, a computer-implemented athletic performance analysis method is disclosed. The method comprises obtaining, at a computer system, first motion data reflecting motion of a sporting device during one or more drills performed by an athlete, and creating and storing action data by identifying a plurality of portions of the motion data, where each of the portions correspond to one or more actions by the athlete. The method also comprises comparing the action data for the athlete, with the computer system, to corresponding aggregated action data for a plurality of other athletes to determine a relative skill level for the athlete with respect to the one or more actions, and generating data for a report that reflects the relative development level of the athlete. The method can also include capturing the motion data with a plurality of motion sensors mounted inside a sporting ball. In addition, the method can include wirelessly communicating the first motion data over a short-range connection to the computer system.

In some aspects, the wireless communicating is instigated by a request from the computer system to a controller in the sporting ball made during period when the sporting ball is not capturing data. In certain aspects, the method can also include determining a relative skill level for the athlete corresponding to a first drill at a computer local to the sporting device, and determining a relative skill level for the athlete corresponding to a subsequent plurality of drills at a computer system remote from the sporting device. The method can also include generating the report to a portable media to be provided to the athlete, such as to paper or a flash memory device. The report can include a ranking of the athlete within a continuum of athletic performance and one or more instructions directed to reducing weaknesses identified in the athlete's performance. Also, the method can include obtaining second motion data reflecting motion of the sporting device during one or more drills performed by the athlete at a time subsequent to obtaining the first motion data, and performing a comparison of the athlete's performance between obtaining the first motion data and obtaining the second motion data.

In some aspects, the method further comprises comparing information from the first motion data and the second motion data to data representing athletic development of an aggregated plurality of athletes, to generate a predicted athletic performance trend for the athlete. The data for the report can also represent an overall skill level for the athlete, and a plurality of levels for each of a plurality of actions that were tested by the drills. In certain aspects, the action data for the athlete and the aggregated action data for the plurality of other athletes is matched to common portions of common drills performed by each of the athletes.

In another implementation, a computer-implemented athletic performance analysis system is disclosed, and comprises a data collection interface in a computer system to obtaining first motion data reflecting motion of a sporting device during one or more drills performed by an athlete. The system also comprises a computer-implemented classifier to compare data corresponding to the first motion data to corresponding aggregated motion data for a plurality athletes to determine a relative skill level for the athlete with respect a determine athletic skill. In addition, the system comprises a report generator to generate data for a report reflecting the relative development level of the athlete. The system can also comprise a classification rules generator to identify common features for athletes of a known skill level and to generate rules for determining how other athlete compare to the known skill level.

In some aspects, the classification rules generator comprises an expert system that identifies common features in motion-related data from the athletes of a known skill level and generates rules that are predictive for classifying other athletes according to the known skill levels. The system can also include a trend generator for analyzing the first motion data form the athlete from a first time period and second motion data from a second time period for the athlete, and comparing differences between the first motion data and the second motion data to trend data for the athletes of known skill level to predict a skill level for the athlete.

In some aspects, the system comprises a client computer subsystem proximate to the sporting device and a server computer subsystem remote from the sporting device, wherein the client computing subsystem is programmed to provide the first motion data to the server computer subsystem, and the server computer subsystem is programmed to provide to the client computer subsystem the data for a report reflecting the relative development level of the athlete. The server computer subsystem can include a demonstration mode in which data for a first drill is analyzed and reported on, and a full test mode in which data for a plurality of drills other than the first drill are analyzed and reported on. Also, the client computer subsystem can include a wireless interface configured to communicate with a motion sensing system inside the sporting device.

In yet other aspects, the system further comprises an accounting module configured to correlate an identity of the client computing subsystem with an account, and to debit an accountholder associated with the account for the report. The report can also include a ranking of the athlete within a continuum of athletic performance and one or more instructions directed to reducing weaknesses identified in the athlete's performance.

In yet another implementation, an article comprising one or more tangible computer-readable data storage media is disclosed. The media contain program code operable to cause one or more machines to perform operations that comprise obtaining, at a computer system, first motion data reflecting motion of a sporting device during one or more drills performed by an athlete; creating and storing action data by identifying a plurality of portions of the motion data, where each of the portions correspond to one or more actions by the athlete; comparing the action data for the athlete, with the computer system, to corresponding aggregated action data for a plurality of other athletes to determine a relative skill level for the athlete with respect to the one or more actions; and generating data for a report that reflects the relative development level of the athlete.

In another implementation, a computer-implemented athletic performance analysis system is disclosed, and comprises a data collection interface in a computer system to obtaining first motion data reflecting motion of a sporting device during one or more drills performed by an athlete; means for identifying a skill level for the athlete by comparing data corresponding to the first motion data to similar data aggregated from a plurality of athletes of known skill level; and a report generator to generate data for a report reflecting the relative development level of the athlete.

The details of one or more embodiments are set forth in the accompanying drawings and the description below. Other features and advantages will be apparent from the description and drawings, and from the claims.

DESCRIPTION OF DRAWINGS

FIGS. 5A-5C are example screen shots from a system that provides reports and recommendations to athletes regarding their athletic performance.

Like reference symbols in the various drawings indicate like elements.

DETAILED DESCRIPTION

Figure 1:
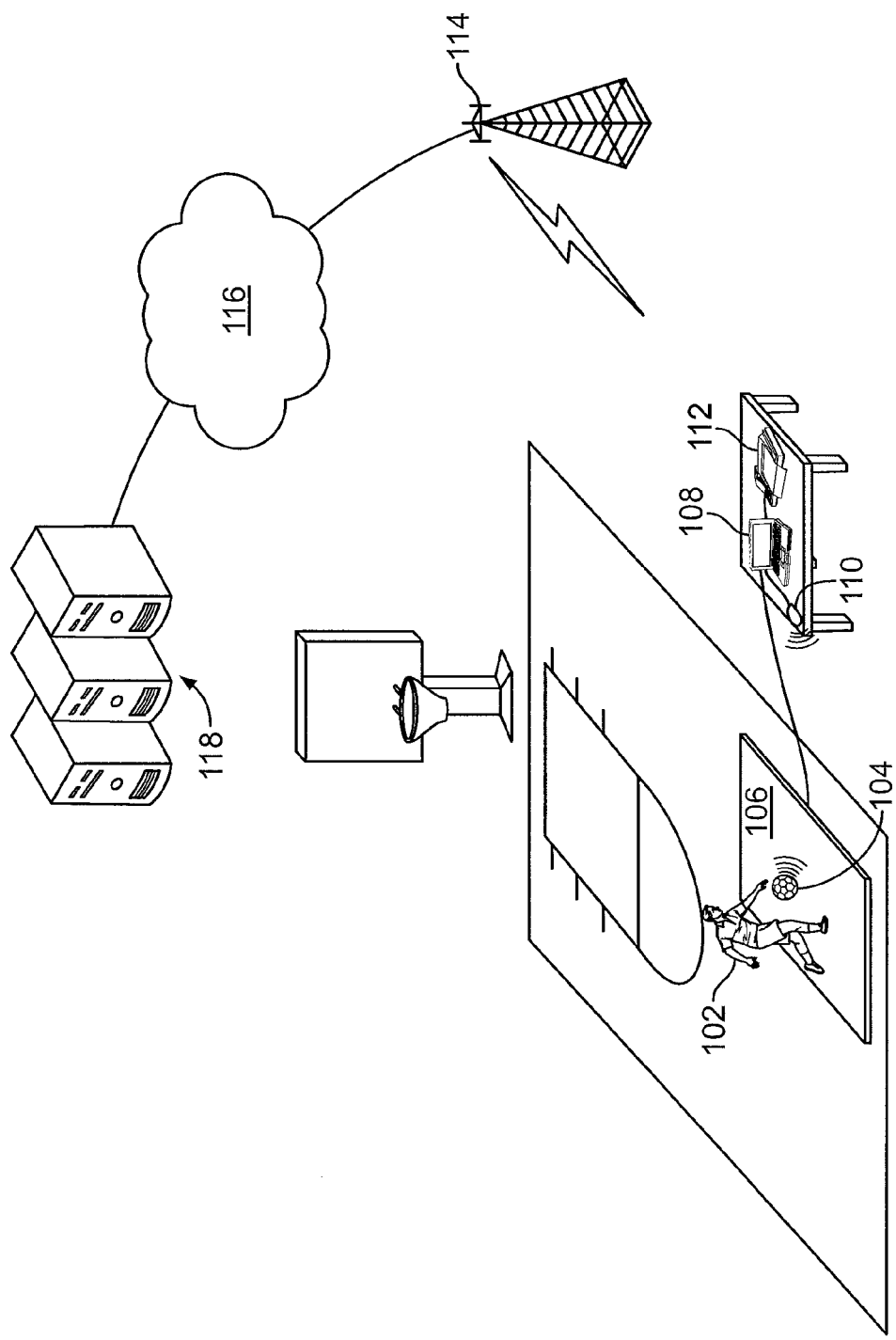
FIG. 1 is a conceptual diagram of a system for electronically measuring athletic performance and providing feedback on the performance.

This document describes systems and techniques for capturing and evaluating athletic performance in a repeatable and objective manner by measuring athletes who have been instructed to perform certain drills that match drills that other athletes have also performed. In general, a sporting device such as a basketball or other ball can be provided with, or be observed by, motion sensors, such as accelerometers and angular rate gyros, to record data about the manner in which an athlete manipulates the sporting device. Additional data may be captured from the athlete, such as via laser-based motion recorders, pressure sensitive pads, and shoe-based sensors. The athlete may be directed through one or more drills, such as a dribbling or shooting drill, and their actions may be recorded through the various sensors as they complete the drill. The drill may be well defined so that the data that is captured may be compared to other instances of the drill, including instances in which the same athlete performed the drill at different periods ion time, and instances in which other athletes performed the drill.

The motion data may be captured on a computer system in proximity to the location where the athlete performed the drill. The capturing of the data may occur, for example, via wireless communication between a sensor assembly inside the sporting device and a wireless transceiver attached to a computer, such as via a USB port or similar interface. The motion data may then be transformed, sampled, and converted in various manners and may be compared to data from other athletes that has been aggregated for later statistical or similar analysis. The other athletes may have provided indications about their level of athletic performance, such as whether they are varsity high school players, junior college players, division I players, professional players, or other levels of player. If those other athletes performed the same or similar drills under controlled conditions (by being instructed by, and observed by, a technician to ensure that they follow the appropriate steps of a drill), their aggregated data can be compared to the data for the first athlete to determine where, on a continuum of skill levels like that just described, the athlete falls.

Such an analysis may be simple, such as by being based on a single drill, or it may be complex and involve a large number of drills that test a variety of skill sets for an athlete. The simple testing may be conducted as an initial test to see if an athlete is interested in further testing. For example, testing may be provided at a public event like an AAU basketball tournament or a 3-on-3 basketball tournament. More complex testing may also, or alternatively, be conducted. For example, athletes may attend more extensive testing at fixed athletic facilities, such as facilities that are relatively common in major metro areas. The additional testing may test a variety of drills that include tests for ball handling, jumping, shooting, and other similar skills.

The test results may be generated at a central facility that is remote from the various test centers. Such an arrangement may permit easy deployment of the system, with sensor-fitted balls and wireless transceivers being the only hardware that needs to be sent to remote sites in many implementations. Client computers such as laptop computers may be provided by a technician, and may communicate with a remote server over the internet, including through a web browser that has a downloaded plug-in for controlling communication with the sporting device and for uploading the gathered information to the server.

The server may in turn include a web server, and the client computer may receive information back in the form of an XML and/or HTML document that can be shown or otherwise provided to the athlete, with a summary of the data that was reviewed for the athlete, and a list of instructions and exercises for the athlete in order for the athlete to address any weaknesses perceived from the testing.

Athletes may also be encouraged to conduct testing at multiple different time periods. Such testing may measure the relative progress that the athlete has made. Such relative progress may also be compared to aggregated data on the progress of other athletes. The evidence of progress for the particular athlete may be fit in a number of known mathematical and statistical manners so as to produce a prediction of the athlete's near term and longer term expected progress if the athlete continues at a pace of development that matches the development measure for other athletes of similar progression.

Referring now more particularly to the figures, FIG. 1 is a conceptual diagram of a system 100 for electronically measuring athletic performance and providing feedback on the performance. The system 100 generally includes a sub-system that is local to one or more athletes who are being tested, and a sub-system that is remote from the athletes and includes one or more servers. Although a separated system is shown here, all of the processing for the system may also be localized at a single location.

A separated system may provide a number of advantages, however. For example, it may eliminate the need to deploy and maintain computers and software in the field. Rather, only limited technology, such as one or more sporting devices (e.g., balls, shoes, clubs, etc.) need be sent out, and software may be downloaded to computers (such as laptop computers) that are already in the field, such as via a web browser plug-in that manages communications with the sporting device and uploads device data. As a result, a company operating the system may reduce its capital costs significantly by using computers that are already owned by field personnel and are being used for other purposes. In addition, the company can better control who is using its technology, by maintaining ownership, for example, of the sporting devices, so that a field representative must return the device when their term of representation is over. Also, when field deployment of software occurs via download over the internet, a company can push out the programs more easily, and may also keep them updated regularly with little effort. Moreover, such a separated system permits the company to maintain better control over its analysis code so that the code is not easily taken and provided to a competitor, and so that it can be updated and kept fresh in a very controllable manner.

A hybrid approach to splitting the duties of the in-field sub-system and a central sub-system can also be pursued. For example, a client device such as a laptop computer may be provided with code and data that is sufficient to test an athlete in one entry-level drill, such as dribbling a figure eight. Such distribution of basic testing code may permit the testing to occur more quickly and reliably than if a round-trip to a central server were required. Such reliability can be important for entry-level testing also, because frequently such testing would occur at various festivals and tournaments that are far from dedicated IT equipment.

In the hybrid system, the server system could be used for subsequent and more extensive testing, after athletes have been introduced to the system and have decided they would like to receive additional testing and guidance. In this manner, the system 100 can be introduced conveniently to athletes and they can be given an inexpensive trial of the system's capabilities with the entry-level drill. Although security may be compromised for testing of the one drill (because the analysis code will have been sent to remote client devices), a competitor could not make much from the one drill in any event, so the risk to security is minimized.

In FIG. 1, the local computer sub-system is made up of a laptop computer 108, a wireless transceiver 110, and a printer 112. The computer 108 may take other forms and may be loaded with software to cause an athlete's data (from the measured motion of a sporting device that the athlete manipulated and/otr other sources) to be analyzed, and may cause reports to be provided to the athlete. The computer 108 may be loaded with native applications to receive such input and produce such reports, and to also analyze the input data with respect to similar data from other athletes. Alternatively, the computer 108 may be loaded with basic workplace applications, such as a web browser, and the system 100 may provide a downloadable plug-in for the browser that will control communications with the transceiver 110 and with a server.

The transceiver 110 may take a variety of forms, and may be directed to capturing motion data from a sporting device in the form of a basketball 104 in this example. The basketball 104 may be of a common size and shape, and may contain a sensor assembly that includes accelerometers and angular rate gyros mounted inside it, in a way that does not interfere substantially with the handling of the ball, to capture motion of the ball 104 in a manner that is usable to the system 100. The transceiver 110 may in turn communicate with the computer 108 in a familiar manner, such as through a USB port or the like, so as to make relatively simple the use of the computer 108 with the system 100 to capture motion data.

The printer 112 is shown as an example of one way in which a report on an athlete's performance can be presented to the athlete. For example, certain numerical figures or graphs may be generated to visually show where the athlete scores on a continuum of skill levels. In addition, recommendations may be generated in a textual format to be given to the athlete, with particular instructions on how the athlete can improve their performance, including suggested exercises or drills to perform in order to improve the athlete's muscle memory for a particular task. For example, if the testing of an athlete indicates that the athlete does not release the ball during a dribble with adequate velocity, the system 100 can recommend drills and conditioning routines to address such a situation.

In addition to being provided on paper from printer 112, information may be provided to an athlete regarding his or her performance via other mechanisms. For example, data for an athlete may be copied to a thumb flash drive or other similar mechanism. The athlete may then return to a next testing session and provide the memory mechanism for use in comparing the athlete's skills at an earlier time to their current skills, and extending out any recognized trends to give the athlete or someone reviewing the athlete an opportunity to see if the athlete is similar in skills to other athletes who have excelled over time, or have stalled and fallen behind comparable athletes.

The data for an athlete may also be stored in the system 100, and the athlete may provide identification information in subsequent visits so that prior test data for the athlete is joined with subsequent test data. Access to data may be provided to the athlete via a message sent to the athlete (e.g., via text message or e-mail) or by providing the athlete with log in credentials to a central site. A combination of such methods for provided the athlete with access to the data may also be employed. In addition, reporting tools may be provided under any of the examples above, so that the athlete may return home and produce custom reports and otherwise manipulate the data on their performance.

An athlete 102 is shown in FIG. 1 dribbling the basketball 104. For example, the athlete may be instructed to dribble the ball in a figure-8 pattern several times, or for a fixed number of times so as to record a statistically relevant sample of items to record and analyze, while motion data is being captured by sensors in the basketball 104 and perhaps via other sensors. The athlete is also shown as performing on a pad 106. The pad 106 may be pressure sensitive and may provide additional data that may be coordinated with the motion data from the sporting device 104. For example, the relative timing between up and down motion of a ball and contact timing of a basketball player's feet may indicate certain room for improvement in the athlete's skill set.

In addition, other sensors may be employed along with the sensors in the sporting device, such as laser location finders that may indicate the relative positions of points on the athlete's 102 body, or motion data of the basketball 104 that cannot be fully captured by sensors inside the ball. Certain sensors may also identify information relating to the actual time that a drill starts and stops, or how quickly an athlete moved from point A to point B while simultaneously controlling the athletic device, how consistently the athlete handles the ball, the variability between dribbles, etc. Also, sensors may be used to determine athleticism, such as in vertical jump tests, both to measure the height of the athlete off the ground and to measure the acceleration of the athlete off the floor.

The sensors may generate a variety of data types. The sensors can measure athletic stride, number of impacts, change of direction, etc, while sensors in a ball would capture the muscle memory skills associated with handling the ball while moving in very quick and short bursts. Also, the timing of data for various sensors may be aligned and synchronized so as to delver more information on the athlete's performance. For example, laser-based sensors, when combined with in-ball sensors, may provide an indication when a player loses a dribble during a drill, even in situations where either sensor group alone would not make the same determination.

Sensor-equipped specialized athletic devices that differ from the corresponding devices that are used in competition may also be used for testing athletes. For example, sensors may be provided in a weighted ball, and an athlete may be directed to execute drills that can deliver predictive or diagnostic data on a player's core strength. For example, the heavy ball can be thrown, and the sensors can capture acceleration, distance, and speed. As another example, an athlete can perform a series of repetitive drills with the torso, such as situps. The sensors can measure force, acceleration or other movements, the average and median of these measurements, and any degradation of these elements over the course of the entire drill. These measurements can be used to benchmark, compare, and predict core athletic strength that is critical in many sports.

Certain of the information may be compared to aggregated data for other athletes, while certain data may be provided in a form that does not involve such comparison. For example, drills for particular skills may be compared to other athletes, while core strength measurements may simply be provided in raw for or in some revised form (e.g., on a scale of 1 to 10) but without the need to place such numbers into some preexisting skill level relative to other athletes. In this manner, various sorts of data may be made available for review by an athlete or by others from a single location—whether the particular data is best presented in comparison or as an absolute.

The local client sub-system may be connected to the server sub-system through a wireless connection, such as an aircard or similar structure or a WiFi card and WiFi hot spot. A network 114, such as a cellular data carrier network 114 may transfer the data and communicate through a network 116 such as the internet, to the server sub-system shown here as a single server 118, but which could include a large number of servers to receive various types of requests. The server 118, as described in more detail below, will have previously been provided with data reflecting skills for a number of other athletes who already ran the relevant drill or drills. The previously processed data will also indicate the skill level of several of the athletes.

The server 118 can thus compare the data representing the performance of one athlete acquired by the client sub-system, to the information that is aggregated for performances of a group of other athletes whose relative levels of development are generally known. The server may then return to the computer 108, through the networks 114 and 116, information that can reflect such a determination and provide additional helpful data and advice to the athlete. For example, the computer 108 may be used to print out a number of pages of mark-up language material (e.g., HTML) that include data and graphs to show the athlete what was measured from them, and what comparable values have been observed for players from various levels of a sport. In addition, various instructions can be provided in a similar manner, which the athlete can take home with them and read to improve a particular skill set or drill. Such data and reports may be provided via printer 112, or via an electronic file such as an HTML or PDF file stored to removable portable media that is given to or provided by the athlete. For example, a sponsor at an athletic event may supply free flash memory containing the sponsor's name, and the data for an athlete may be stored onto the flash memory by attaching the flash memory in a well-known manner (e.g., through a USB port).

An athlete can also capture data to be used in customizing a videogame experience. The athlete can first perform a variety of drills to obtain statistics indicative of their overall current skill levels in a sport. They may then have the figures loaded to portable memory devices that can be used with videogame systems, whether console or PC. Such athletes may then load the data to a game that involves an athletic performance that uses the skills tested by the athlete, and their character or avatar in the game may perform according to their actual real-world skill level, with multiple different variables being identified to define the full performance palette for the athlete. In this manner, friends may set up head-to-head battles in sporting games, where their own personal skill levels affect how the simulated videogame contest will turn out. The athletes may also thus be motivated to return for additional testing after they have practiced so that they can have better baseline skill numbers that will improve their performance vis-a-vis other players in the game.

Figure 2A:
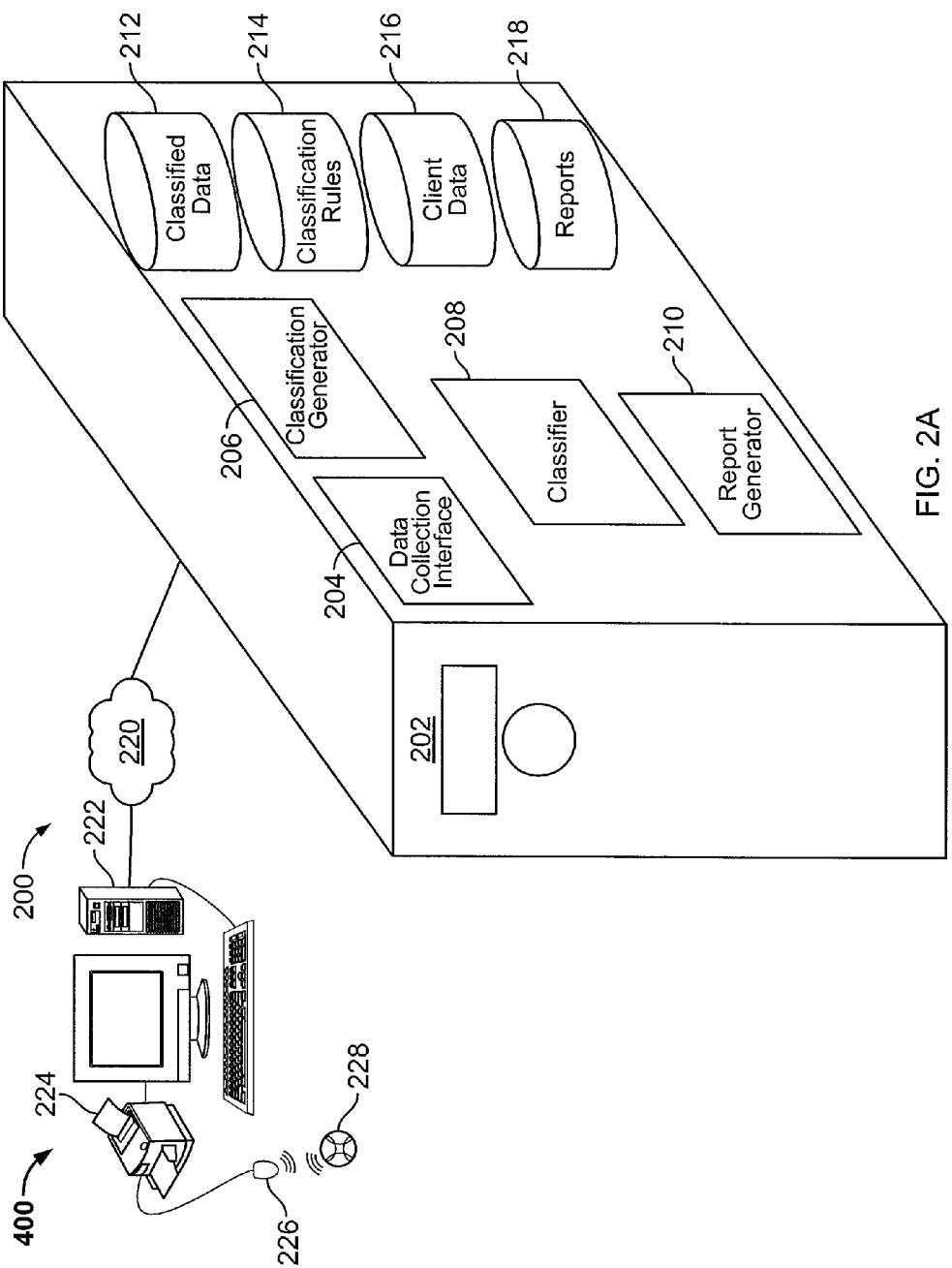
FIG. 2A is a block diagram of an illustrative computer system for comparing performance indicators for an athlete to aggregated performance indicators for a plurality of other athletes.

FIG. 2A is a block diagram of an illustrative computer system 200 for comparing performance indicators for an athlete to aggregated performance indicators for a plurality of other athletes. In general, the system 200 is similar in arrangement to system 100 in FIG. 1, but more detail is shown here about a server system 202 that may be used to provide evaluation data for athletic performance.

Starting at the client side and then moving to the server system 202, there is shown a sporting device in the form of a basketball 228, which may communicate motion data that is measured by sensors inside the basketball 228 with a wireless transceiver 226. The wireless transceiver 226 may in turn provide the motion data to a computer 222 that may pass the information to a network 220 such as the internet and/or a wireless network like a WiFi network or cellular data network, and on to the server system 202. The computer 222 is also provided with one or more output devices in the form of a printer 224 and computer monitor, and may also have ports for writing to portable memory devices carried by athletes who are tested by the system 200. The client-side system in this example can be operated in a manner similar to the system 100 described in FIG. 1.

On the server side (which again, may include one or a number of server computers, including web servers, database servers, and other computers), the server system 202 includes a number of components to assist in processing data regarding athletes' performance in a number of drills. (which may be among a number of additional components that are omitted here for clarity)

First, a number of data stores 212-218 hold data that is relevant to the athletic evaluation functions. For example, a classified data store 212 includes information from past athletes whose performance data has been generated and who are classified into certain skill levels. The data may be aggregated from across a large number of athletes so as to make the data meaningful. Also, each set of data may be correlated to a particular drill or exercise performed by the athlete, so that the data can be properly compared to data for other athletes that performed a matching drill or exercise. (A matching drill is a drill that is the same as a first drill or that includes some substantial superset or subset of the first drill.)

Classification rules dataset 214 may store data representing rules that are derived from analyzing the classified data, and may include heuristic rules or other rules to apply to incoming data to determine an appropriate skill level of an athlete who generated the data. For example, a set of rules may be combined to determine a skill level of a freethrow shooter, such as the number of times a free throw rotates and the hangtime and entry angle of a free throw.

Client data datastore 216 may store two or more types of data. For example, it may store information about the particular client computer 222 that is sending testing data to the server system 202, such that an account associated with the computer 222 or with a login made through the computer 222 can be debited. Such debiting may occur where an operator of the client system collects money for providing the testing services, and some of the money is to then be provided to the organization running the server system. In such a manner, the central system may best be able to audit the operations of field personnel and to track accounting functions properly (because it will know the number of transactions). The client data may also relate to athletes that have used the system 200. Such client data may include raw motion data that has previously been uploaded in combination with an ID for the particular athlete, in addition to a history that summarizes tests and drills the athlete has completed, and reports and recommendations that have previously been provided to the athlete. Storing such data may permit the system 200 to provide ongoing support to an athlete as they develop, including by providing reports that show past progress of the athlete at certain tasks, and projections for the athletes' development with respect to those tasks.

A reports data store 218 stores formats for various reports that may be provided to athletes or advisers to athletes. The reports may take a variety of forms, such as tabular data comparing an athlete to other athletes or groups of athletes, graphs making similar comparisons, and textual reports providing recommendations for drills and exercises that an athlete may undertake to improve his or her performance (See, e.g., FIGS. 5A-5C). In addition, the reports can include tracking modules that can be downloaded to a portable media owned by the athlete, where the athlete may track developmental milestones using the modules. For example, an athlete can enter the completion of certain exercises and the results of exercises that the athlete has completed, and the module may communicate with the system 200, either immediately (e.g., to schedule follow up testing when the athlete's results indicate that they may be ready to enter a new level of development) or the next time the athlete comes in for testing. Tracking actual activity of the athlete may improve the advice given to the athlete. For example, if the data indicates that the athlete has worked very hard on a particular skill set or muscle group, but is not showing development at a sufficient level, the routine for the athlete may be changed by identifying the athlete as sharing characteristics with a different group of athletes who previously responded poorly to one routine, but responded better to a different routine.

Other components shown in the figure provide particular functionality for the server 202. For example, a data collection interface 204 may obtain uploaded data about athletic performance form the computer 222. Such an interface may take a variety of forms, including as a web server that serves forms that a technician may fill out for each athlete (e.g., to include identification information and information about the drill or drills performed by the athlete), and that include selectable controls that cause data from the basketball 228 to be gathered and then uploaded to server system 202.

The data collection interface 204 may also screen uploaded data to ensure that it matches an appropriate profile for any particular drill that the data supposedly represents. For example, the interface may test to ensure that the data represents a long enough time period, an appropriate number of dribbles, appropriate motion data for the drill (e.g., there should be some bouncing for a dribbling drill), and may provide an alert back to a technician (e.g., to repeat the testing) if the data does not appear to be proper data.

A classification generator 206 develops rules for placing athletes into particular rankings or classifications relative to other athletes of known classification. The rules are selected so as to provide statistically predictive indicators of real athletic performance that can be derived from motion data and other data compiled from athletic drills. The classification generator 206 may, for example, receive motion data from a large plurality of athlete who have been classified as falling into particular skill levels. The classification generator 206 may analyze the data in various known mathematical manners to identify correlations between data points for athletes of a particular skill level or similar skill levels. For example, the classification generator 206 may recognize that athletes of a particular skill level frequently dribble a basketball according to a particular time pattern, or that the ball spends a certain amount of time cradled in their hands during a dribbling exercise. Where the athletes provided their data in a controlled manner by conducted a predefined and repeatable drill, such correlations can be determined to have significance, and can then be made into classification rules by the classification generator 206.

The rules for classification may also be generated with manual input. For example, an operator of a system may determine particular aspects of performance that have been correlated with an athlete's skill level. They may then test a number of athletes at known skill levels to identify values for that aspect of performance at each skill level (and to confirm that there is a correlation between the values of the aspect and skill level), and may store the measured figures for that aspect of performance.

A classifier 208 in the system 200 uses such rules, in whatever form they may be provided, to classify future athletes according to the strengths, abilities, and weaknesses. The classification may occur according to heuristics, by a degree-of-match determination across multiple factors to corresponding data for athletes of known skill level, or by other acceptable mechanisms. Such classification may occur by obtaining data relating to measured motion data for a new athlete in predefined drills that correspond to the drills performed by the prior athletes of known skill level.

The classifier 208 may also include a trend analyzer that may correlate an athlete's data at different points in time, to the performance data of other athletes at different points in time. Thus, the other athletes may have been tested over time, and may be provided with identification numbers so that the different testing can be matched (though the identities of the athletes themselves may be anonymized). Various trending techniques may be performed to find prior athletes who trended in particular manners for one skill or a predefined group of skills that has been determined to develop in parallel. The new athlete may also provide information about their skill level, which information may be fed back into the system 200, where the new athlete will joint the ranks of the preexisting athletes of known skill level. Classification and comparison may thus be completed again to strengthen the system's rules as time moves on and additional athletes are added to the system.

A report generator 210 may take raw data from the classifier and merge it with format data from the reports data store 218. Various pre-existing report formats may be used, and each athlete may be provided with a variety of reports, where the number and detail of the reporting may depend on a level of service purchased by the athlete. For example, basic data from a number of athletes for a particular skill may be pulled from the client data data store 216 (along with indicators of the skill level of the athletes), and corresponding data for the current athlete may be placed in line with that other data. The current athlete may thus readily see how he or she stacks up relative to others in skill level, and with respect to the particular drill. For example, an high school athlete may perform at a division II college level for a certain drill and may readily see how they fit with other division II players in that regard, though they may match to junior varsity players with respect to another drill or skill set. Such feedback can be very helpful is letting the athlete determine where they should focus their training.

An athlete can also identify a group with which they would like to be compared. For example, a high school athlete may wish to be compared to all other athletes who have tested on the system in their region or section. Or they may wish to be compared to other athletes on their team. Such identifications of athletes as belonging to certain geographical groups may be used in addition to identifying them as belonging to certain developmental groups.

Also, an athlete can provide information to third parties to permit access to part or all of their testing data. For example, an athlete who is testing at a division II level on certain skills may provide access to a recruiting coach at a division I school to show the coach how the athlete has made great strides in those areas, and thus will be at a division I level by the time they start playing college sports.

Thus, by using system 200, various athletes can obtain both quick and minimal feedback, and longer and more in-depth feedback, on their athletic performance in a convenient manner. The system 200 may provide objective reviews for certain aspects of athletic performance that may then serve as a baseline for more objective review of the athlete (e.g., where tests do not reflect heart or leadership ability).

Figure 2B:
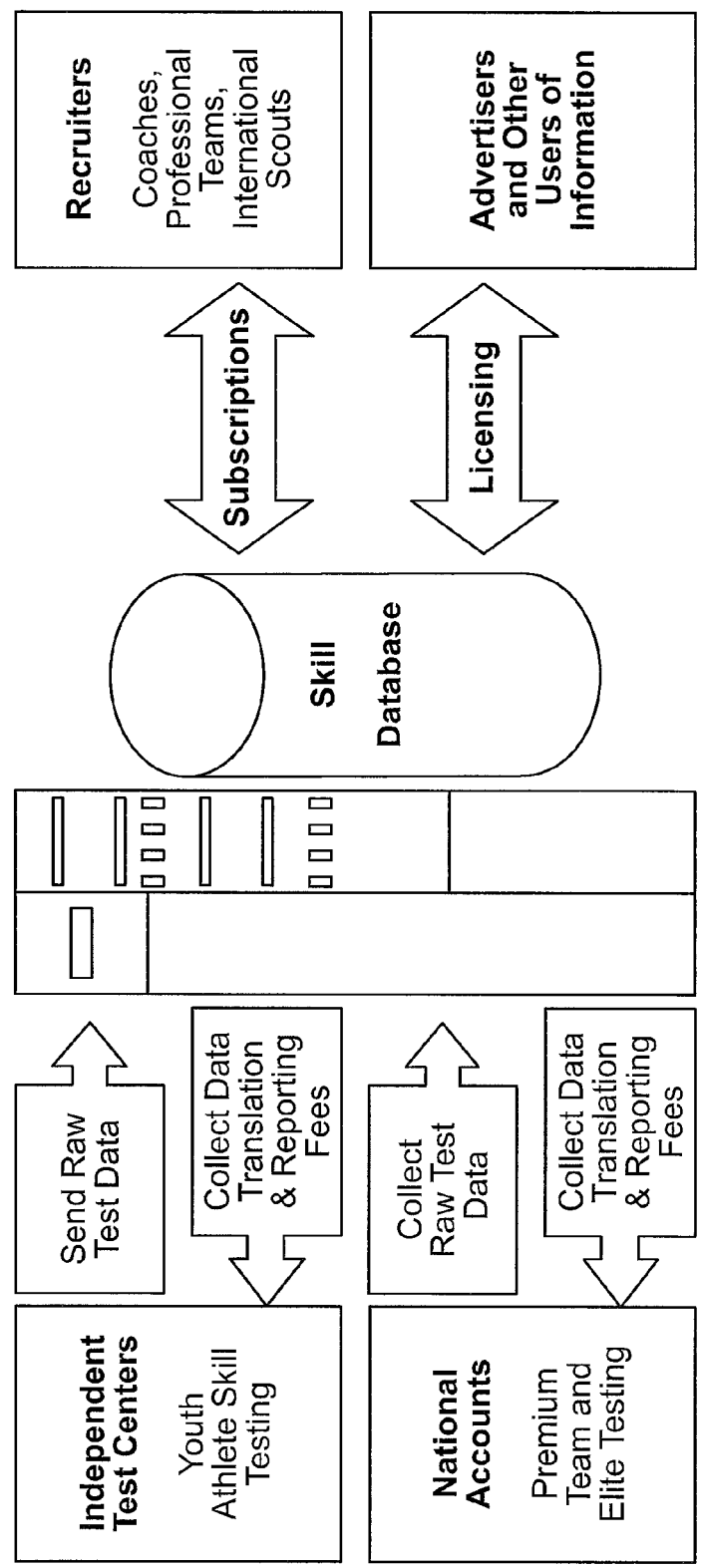
FIG. 2B is a block diagram of a computer-based system for evaluating athletic performance.

FIG. 2B is a block diagram of a computer-based system for evaluating athletic performance. The system in this example is similar to that shown in FIGS. 1 and 2A, but is focused more on the organization of an operational system rather than on the technical provision of data to athletes. The system is focused around a skill database. The skill database stores data of various kinds that reflects performance of a large number of athletes of different skill levels for a number of consistently-applied drill and other activities. The data may reflect, for example, motion data collected from sensors in an athletic device that is separate form an athlete, such as a soccer ball or basketball, and sensors attached to the athlete, such as on a vest or in a shoe or shoes. Certain of the athletes represented in the skills database may have their relative skill level associated with each round of testing, such as according to gross levels (e.g., grade school, high school, college, professional, etc.) or at a more detailed level (e.g., ranked at many levels, and perhaps having different ranks for different drills or skill sets). Other of the athletes may not have an assigned skill level, but may instead be looking to have the system tell them where they stand with respect to the skill levels of other typical users.

Testing and reporting for athletes is shown to the left of the skill database. In this example, two types of operators are identified as having access to the skill database for providing athletes with evaluation data. First, independent test centers may provide testing and evaluation to members of the general public. They may have client systems like those discussed above, to collect the data from athletes such as youth athletes at camps, performance improvement centers, and the like, and may deliver reports and recommendations to the athletes. They may also collect payments from the athletes and remit portions of the payments to an operator of the skill database.

The second type of operator is the national accounts operator. Such operators may provide premium testing services and may be more closely tied to an regulated by the operator of the skill database. Such operators may visit important accounts such as college sports teams, and may conduct mass testing of athletes for such teams. Again, they may provide the raw data for the testing to the operator of the skill database, and may receive report and recommendation data in return. In such situations, the reports may be more detailed, and may also include grouped reporting functionality. In particular, if a team is tested and the testing indicates a pronounced occurrence of a certain weakness in members of the team, the coaching staff or conditioning staff may add drills or exercises to address the weakness on a more global scale, rather than simply for a particular athlete.

The skills database may also be accessed, sometimes for a price, by other organizations that do not collect data on athletes, as shown to the right of the figure. First, recruiters may access data in the skill database to help them make decisions about recruitment. Each athlete may identify, to the system, the schools to which they are applying, and each of the recruiters for such schools may register with the system in a manner that identifies them as being related to their school, and thus gives them access to data for athletes that have identified themselves as being interested in the school. The recruiters may be provided with tools that allow them to see testing scores for various athletes side-by-side, so that they can better compare their prospects.

Athletes may also include ancillary data for such a system, to be reviewed by recruiters. For example, each athlete may be provided with a preformatted home page where they can post information about their academic success (e.g., their grades and volunteer work) and video highlights of their play (or links to video sites that house the highlights). Links may be provided to such pages so that recruiters may obtain a more complete picture of a recruit. In this manner, the system can serve as a national clearinghouse for athletes interested in collegiate opportunities.

As shown in the figure, advertisers or other third parties may be interested in accessing the system. Advertisers, for example, may wish to promote products, such as sports drinks, to user who access the system. In addition, advertisers may wish to identify athletes that identify themselves as using the advertisers' products so as to establish a connection between exceptional performance and the products. In addition, advertisers may wish to review anonymized athletic performance information to determine where in the country certain users are most interested in such testing, so that the advertisers may target their budgets to such areas.

Figure 3A:
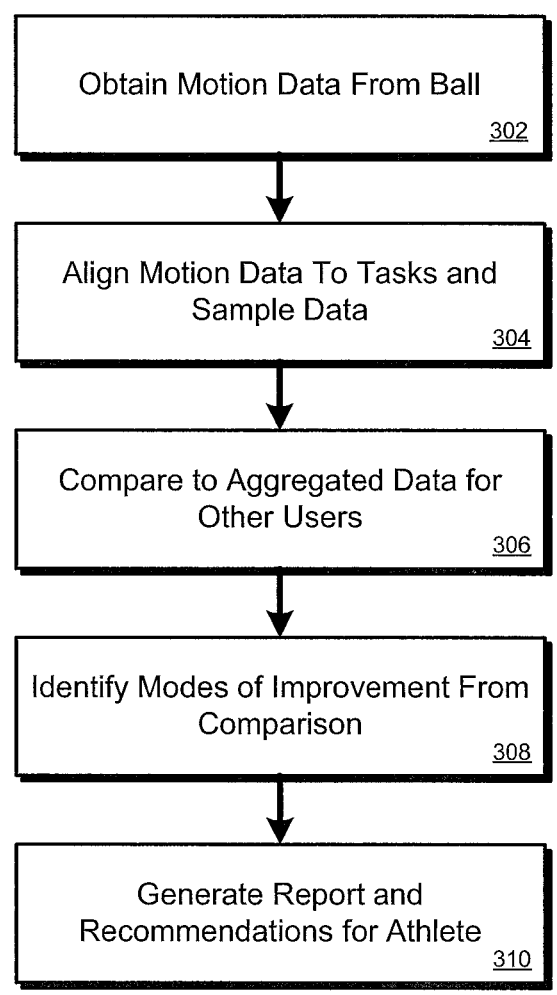
FIGS. 3A and 3B are flow charts of example processes for obtaining motion data relating to an athlete's performance and providing reports and recommendations in response to the athlete.
Figure 3B:
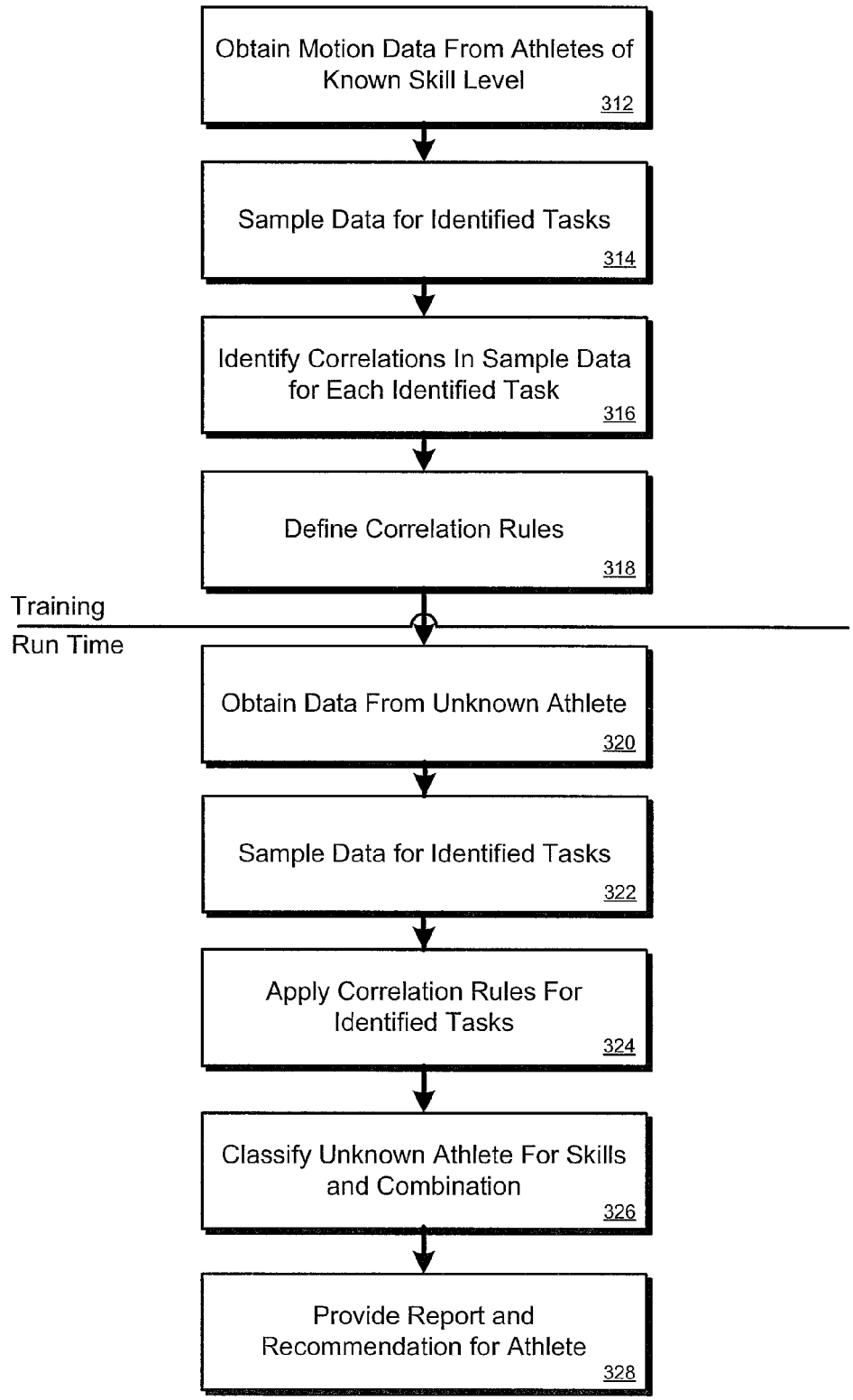

FIGS. 3A and 3B are flow charts of example processes for obtaining motion data relating to an athlete's performance and providing reports and recommendations in response to the athlete. FIG. 3A generally shows actions for testing an athlete and then providing a report and recommendation to the athlete based on that testing. FIG. 3B generally shows a two-part process of obtaining testing data for certain athletes so as to train a system, and then obtaining testing data for other athletes so as to slot those later athletes into an appropriate skill level based on the data that has previously been obtained.

Referring now to FIG. 3A, a first action involves obtaining motion data for an athlete from a ball or other athletic device, in addition to other data describing an athlete's performance (box 302). The action of obtaining the data may involve a server system communicating with a client computer like that discussed above to obtain information for an athlete. The gathering of the information may first have involved registering the athlete into a system such as one of the client systems discussed above, and then having the athlete perform a predefined drill while sensors collect data on the athlete's performance. Sensor systems may have stored the data and then relayed it to the client computer. Where there are multiple sensor systems, the client computer may have combined the information and forwarded it to the server system.

At box 304, the motion data is aligned to particular tasks and is then sampled. For example, in a free throw shooting exercise, player may dribble the ball one or more times before shooting and may pause different amounts of time before shooting. Such delays need to be normalized out of a system so that common parts of the drill may be compared as between multiple athletes. Also, all of the data in the drill is not relevant to all analyses. For example, one analysis may be interested only in the amount of time a ball stayed in a player's hand during a dribble, so the multiple instances of such activity may be extracted or sampled from the raw test data.

At box 306, the athlete's data is compared to aggregated data from other athletes. These other athletes may have provided a system with their current skill levels, and thus, the athlete under test may be placed in a skill level of other users who had similar performance on the particular drill. Certain aspects of the drill (e.g., time in hand for a dribble, number of bounces of the dribble, etc.) may be combined to reach a composite evaluation, and data from multiple drills may also be combined (e.g., for ball handling characterization under a number of different situations).

Modes of improvement are identified from the comparison at box 308. For example, if a dribbling exercise indicates a muscular weakness in a player (because release velocity is lower than normal), the system may identify a weightlifting regimen that has been determined to strengthen muscles related to release velocity. Other modes of improvement may also be identified, and actions to result in the improvement may be found.

At box 310, a report and recommendations for the athlete are generated. The report and recommendations may be in the form of an electronic document, such as an HTML document, that displays data for the athlete's testing regimen along with data for comparable athletes who have undergone the same regimen. In addition, graphical comparisons may be made, and text write-ups may be provided from pre-existing modular report components to give the athlete advice on steps that they can take to improve their athletic performance.

In FIG. 3B, training of a system is followed by testing of an athlete of unknown skill or skill level. At box 312, motion data form athletes of known skill levels is obtained. Such data may be generated by having the athletes complete questionnaires about their level of play (e.g., are they in high school, are they all-conferences, what is their scoring, assist, and rebound average, etc.) and then running the athletes through predetermined drills while collecting data regarding the athlete's performance in the drills, such as motion data of a ball manipulated by the athletes. Each of the athlete's data 314 may then be parsed for analysis, such as by aligning the data and sampling the data for the portions of a drill that are relevant to a particular task. In this manner, the data may be prepared for an accurate apples-to-apples comparison between and among different athletes.

At box 316, correlations are identified for sampled data for each task on which the system is testing. The tasks may be pre-identified by operators of the process, such as when it is known that a certain parameter closely correlates with improved athletic performance.

In other situations, experts systems or other learning systems may be used to identify correlations in data, and thus to identify correlations that operators of a system may not have previously recognized as being correlated to improved athletic performance. For example, perhaps certain top level athletes have a particular hitch in their dribble that allows them to control a ball better without being called for carrying it. Such a hitch may be imperceptible to human observation but may be picked up by motion sensors, and identified by such a learning system.

Where the identified correlations are strong enough to infer some level of causation between the tested factors and actual athletic excellence, correlation rules may be defined, at box 318. These rules may take into account a number of factors form the observed athletic performance data and may generate one or more indicators of true athletic performance for comparison to other test data.

Various machine learning techniques may be used to develop rules that best match correlations that appear in the data of athletes having known skill levels. For example, various well understood techniques may initially be employed to identify aspects of the motion data that may be indicative of performance. Data for those particular aspects may be isolated by aligning the data for different athletes and then focusing on a time window immediately around the relevant data.

With such sampled data points identified, the data may be used to train a classifier system. For example, a number of candidate weak classifiers may first be identified, where weak classifiers can be analogized to small rules of thumb that may or may not be predictive of performance, but are at least somewhat predictive in some circumstances. The weak classifiers may be recursively applied to examples of the sampled data using a boosting technique, such as Adaboost, to develop a strong classifier that may be a combination of the weak classifiers that have been determined to be "best." Additional post-processing clean up may also be performed on the data to better develop a strong classifier.

After this training period on the dats from athletes of known skill level, the strong classifier may be applied to data from athletes of unknown skill level. Such a process may be used to fit the new athlete into the prior athletes so that a strong, objective comparison can be made by the system. Other various known techniques for identifying appropriate portions of the data set to test, and for fitting that data for a subsequent user with data for prior users may also be employed.

The data developed thus far may then be used in a run time phase to measure the performance of other athletes. At box 320, data for such an unknown athlete is obtained, and at box 322, the data is parsed, filtered, or otherwise sampled, in a manner that matches that for the prior athletes in box 314. The correlation rules defined in box 318 may then be applied for the identified tasks to the data for the unknown athlete (box 324). The rules may then place the unknown athlete within performance indicators for athletes of known developmental or skill level (from the first phase), and the unknown athlete may be classified as having a skill level comparable to those other athletes (box 326). Finally, a report and recommendation for the athlete may be provided (box 328). The report may be provided, for example, from a server system over a network to a client computer, and may in turn be provided from there to the athlete for their review.

Figure 3C:
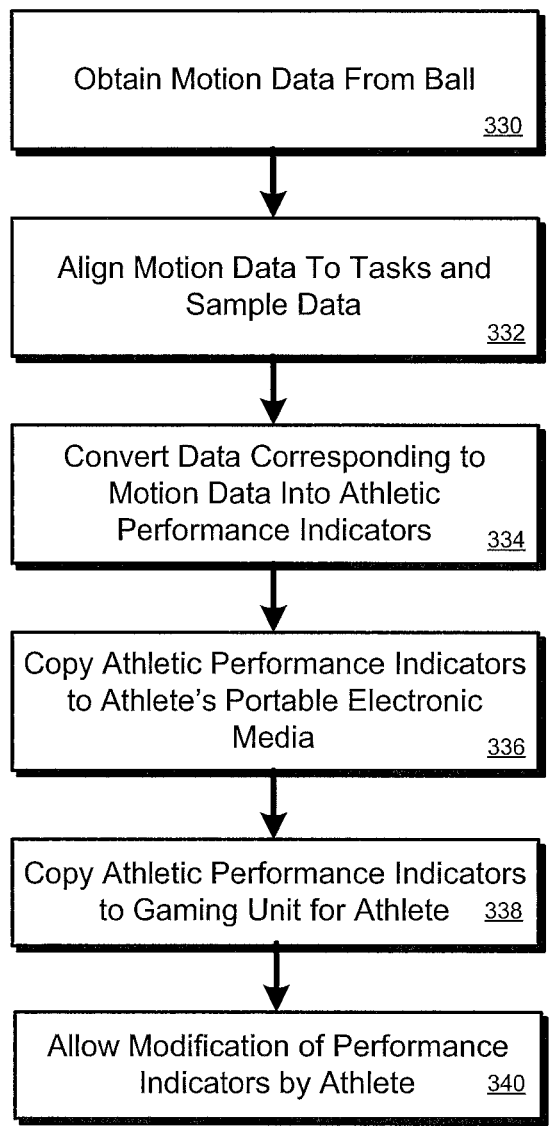
FIG. 3C is a flow chart of a process for capturing athletic performance data for use with a videogaming system.

FIG. 3C is a flow chart of a process for capturing athletic performance data for use with a videogaming system. In this example, the videogame will be a playground basketball game for one-on-one or two-on-two play. The system may be enhanced by defining the abilities of each player in the game according to the real-world abilities of the person controlling the player. Thus, for example, if one person dribbles strong to the right and weak to the left, their avatar in the game will do the same. Such a system may be particular interesting to players, as it recreates real world head-to-head competition but in a more convenient format (e.g., players can play at night after a gym is closed, and over a network from their respective homes).

At box 330, motion data from a ball and/or other sources is obtained for a particular player, such as in the manners discussed above. At box 332, the motion data is aligned to particular tasks (e.g., ball release on a dribble) and is sampled for the particular task. At box 334, the motion data is converted into athletic performance indicators, as in manners like those discussed above. Thus, for example, a player may be given a score from 1 to 100 for certain aspects of basketball play, such as a "first step" speed to the left and the right. Such scores may be stored as parameters for predefined fields that are supported by a videogame for the users. At box 336, the indicators are copied to a portable media of one of the players, such as to a flash memory by a client computer like that shown above, or by network download from a system such as that shown in FIGS. 1, 2A, and 2B. The player/athlete may then carry the portable storage media to their gaming system (unless a network download occurred directly to the system), where the parameter values may be loaded into a game in a familiar manner. At box 340, the performance of an avatar in a game is modified using the performance indicators derived from the player's actual testing.

Figure 4:
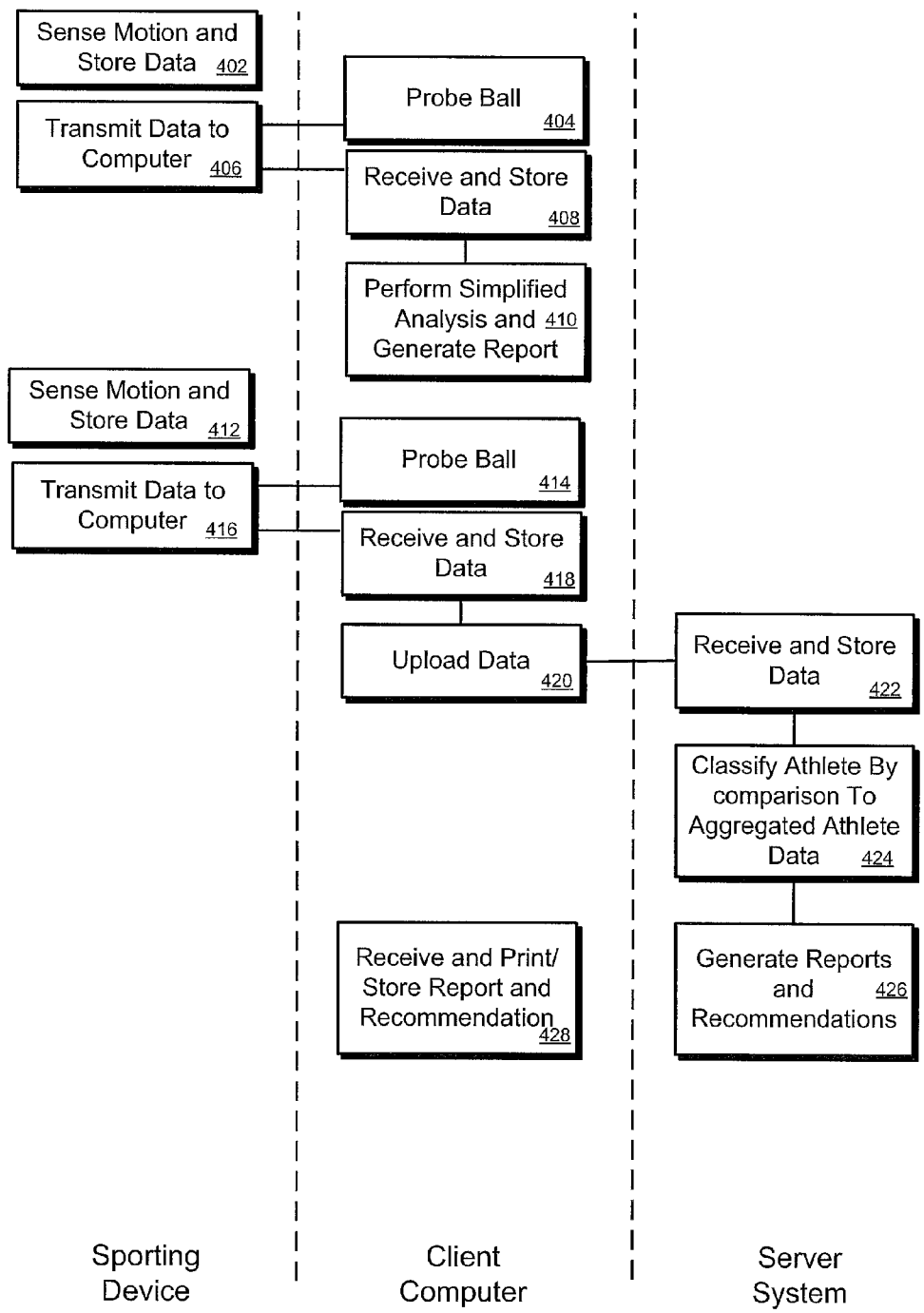
FIG. 4 is a swim lane diagram showing actions taken by components in measuring individual athletic performance and comparing it to group athletic performance.

FIG. 4 is a swim lane diagram showing actions taken by components in measuring individual athletic performance and comparing it to group athletic performance. The particular actions are similar to those discussed above, but show an example of how particular actions may be performed by various portions of a system. At box 402, motion for a drill is sensed and motion data is stored (e.g., from an in-device sensor assembly and/or from sensors outside the device). At some later point, such as after the drill or drills are complete, the client computer probes or interrogates the ball (box 404) and the ball responds by transmitting the data to the computer (406).

The computer than receives and stores the data (box 408). The drills represented by the data may have been performed in a particular order according to a program being followed by the technician that is running the system and instructing the athlete. Thus, if multiple drills were performed, that may be parsed out into their individual components at this or another stage for more accurate analysis. At box 410, the client computer performs a simplified analysis and generates a report. Such actions may simply include posting the athlete's identifying information into a ranking of skill levels that may be displayed on a tote board at the site of the testing. Such posting may allow athletes at a competition to see where they stand relative to other athletes that have tested at the same event, and may encourage other athletes to try the testing service.

The remaining boxes show actions at a subsequent time, such as several days after the first actions. At box 412, motion is again sensed relative to the athlete's performance, and motion data is stores. At box 414, a client computer (which may be the same as or different than the client computer in the first instance) may probe the ball, the ball may in turn transmit the data (box 416), and the computer may receive and store the data, perhaps including by parsing or otherwise reformatting the data (box 418). In this instance, the drills that were tested are more extensive than in the first instance, so the client computer uploads the data (box 420) to a remote server system that in turn receives and stores the data (box 422). The server system may associate the data with multiple identifiers, including an identifier for the athlete (so that the athlete's data may be compared to other data on that athlete so as to judge the athlete's progress) and for the operator of the client computer (so that appropriate accounting activities may take place relative to that entity).

At box 424, the server system classifies the athlete in comparison to other athletes using aggregated athletic performance data for those other athlete performing matching drills at a prior time period. Such classification may occur, for example, using the techniques described in detail above. The server system may also generate information to be reviewed by the athlete or a third party, such as reports and recommendations (box 426) and may, in appropriate implementations, return that information to the client computer, where it may in turn be provided to the athlete in various manners (box 428). The information may also be returned to the client directly, such as by the client accessing a message sent by the server system and/or by the athlete logging into an on line account with a company that operates the server system.

Figure 5B:
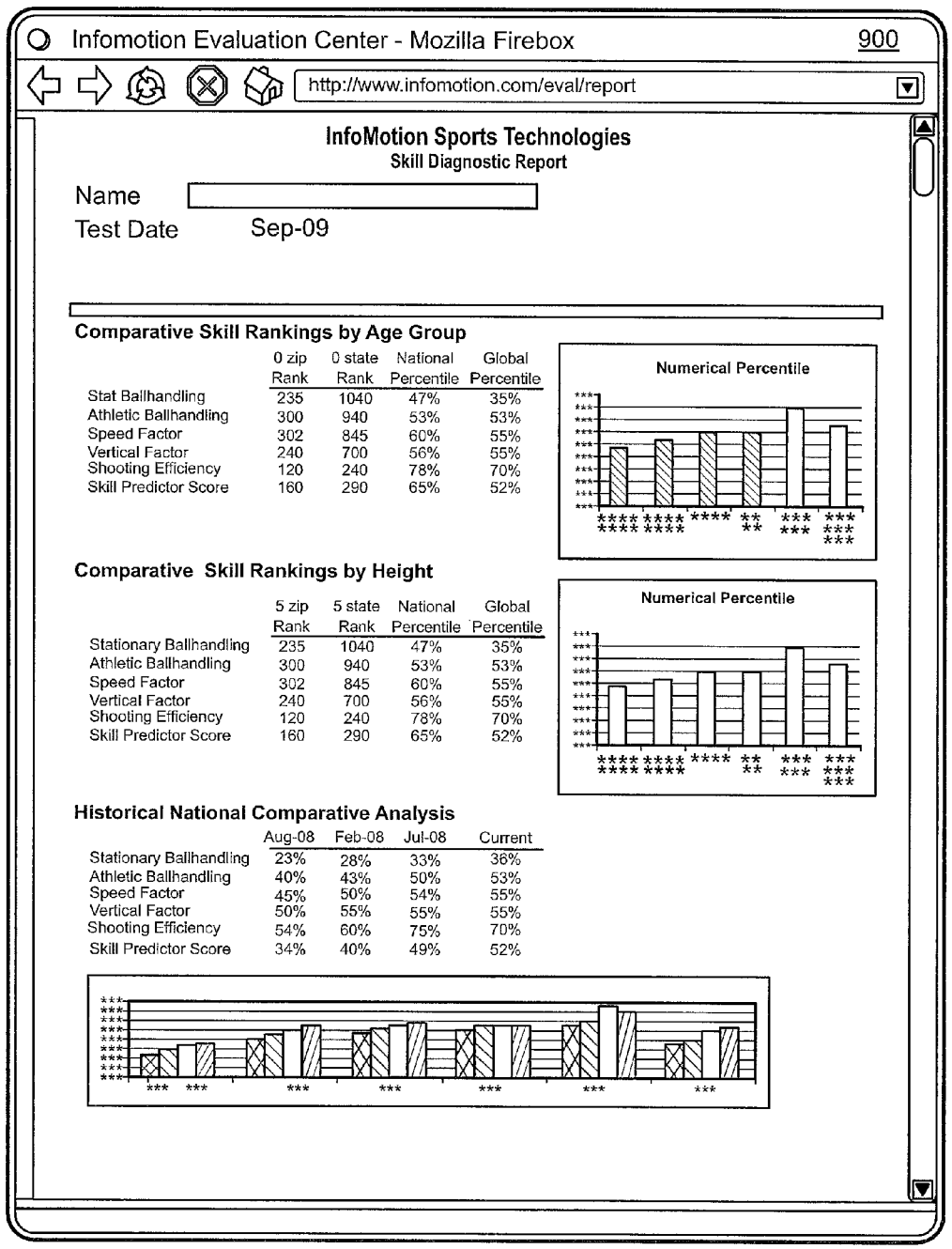
Figure 5C:
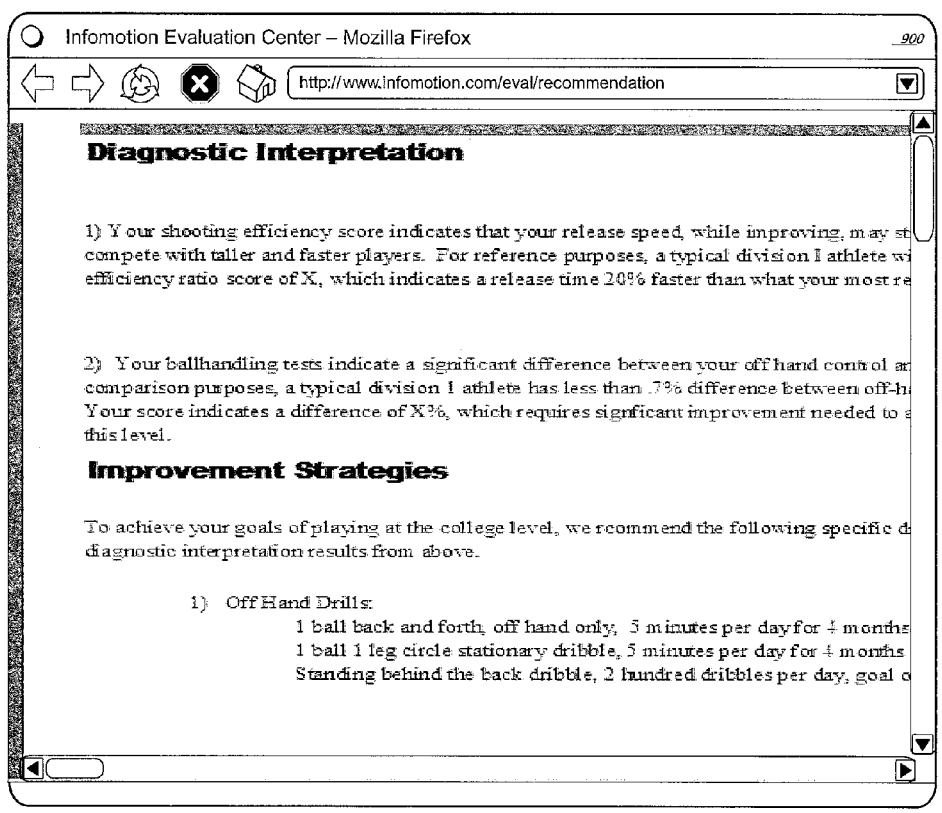

FIGS. 5A-5C are example screen shots from a system that provides reports and recommendations to athletes regarding their athletic performance. In FIG. 5A, data is shown in a general tabular reporting format for testing at different points in time for a number of drills. The athlete can review such data to see where they stand vis-á-vis other athletes and to see their relative progress over time. The report first provides a number of general descriptive figures at the top, to provide some background on the athlete. The report them shows testing data for various skill sets, including some that are aimed more directedly at core athleticisms and others that are directed to finer skills. A skill prediction is provided in a familiar form, with an indication of how string the data indicates such a prediction to be, At the bottom of the report, development of the particular athlete is shown, where the athlete has been tested multiple times.

In FIG. 5B, the athlete's comparison to other athletes is a central focus. The athlete is shown data that describes how they compare to various percentiles of other athletes at the competitive level. The comparison can be cut along different dimensions, such as age group, height group, and geographic zones (e.g., local, regional, state, and national).

In FIG. 5C, a textual recommendation is provided to the athlete, so that the athlete may review it and train to improve weaknesses that the system identified in their performance. Here, the system recommends additional work directed to improve the speed with which the player releases a jump shot, among other things.

Figure 6:
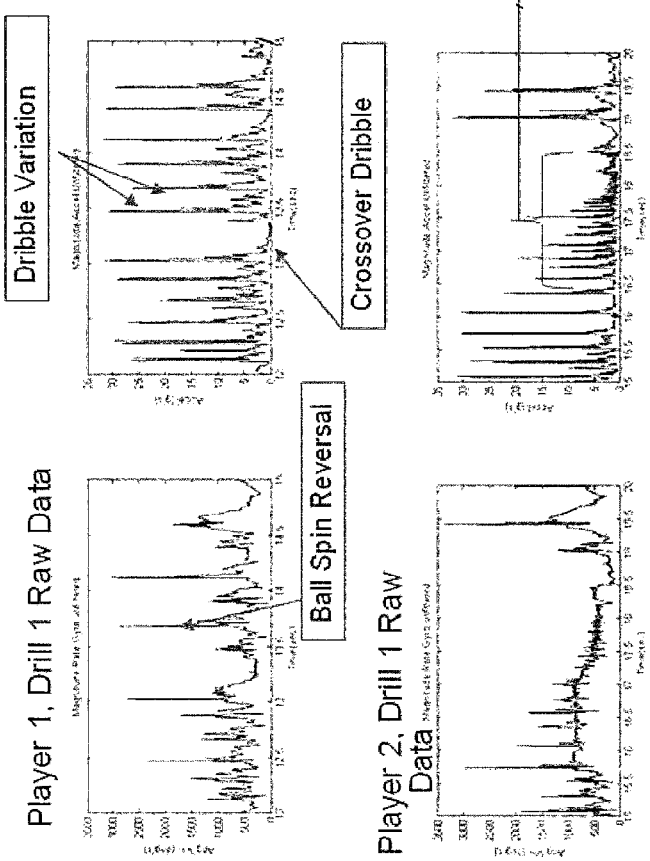
FIG. 6 shows example athletic performance data.

FIG. 6 shows example athletic performance data collected from players performing a basketball drill using a basketball having three gyro sensors and three accelerometers. One gyro sensor records and reports tilt, a second records and reports pitch, and a third records and reports yaw. The three accelerometers record and report acceleration measured in g forces in all three planes. The gyro sensors and accelerometers can be configured onto a circuit board that is placed into an athletic device (e.g., a basketball) in a manner such as those described in U.S. Pat. Nos. 7,021,140 and 7,234,351.

The data regarding tilt, pitch, and yaw can be compiled to create a spin composite as shown in the first column of panels (top and bottom) of FIG. 6. The spin composite allows for the detection and assessment of spin reversals. The data regarding acceleration can be compiled to create a force composite as shown in the second column of panels (top and bottom) of FIG. 6. The force composite allows for the detection and assessment of acceleration forces placed on an athletic device in three different axes. The spin and acceleration composites can be used individually or in combination to provide performance information about a player's ball handling, ball shooting, and ball kicking (in the case of soccer) abilities. The top panels (player #1) show the spin composite data and the acceleration composite date for a division II player having superior muscle memory and ball handling ability. The bottom panels (player #2) show the spin composite data and the acceleration composite date for an average high school player.

Figure 7:
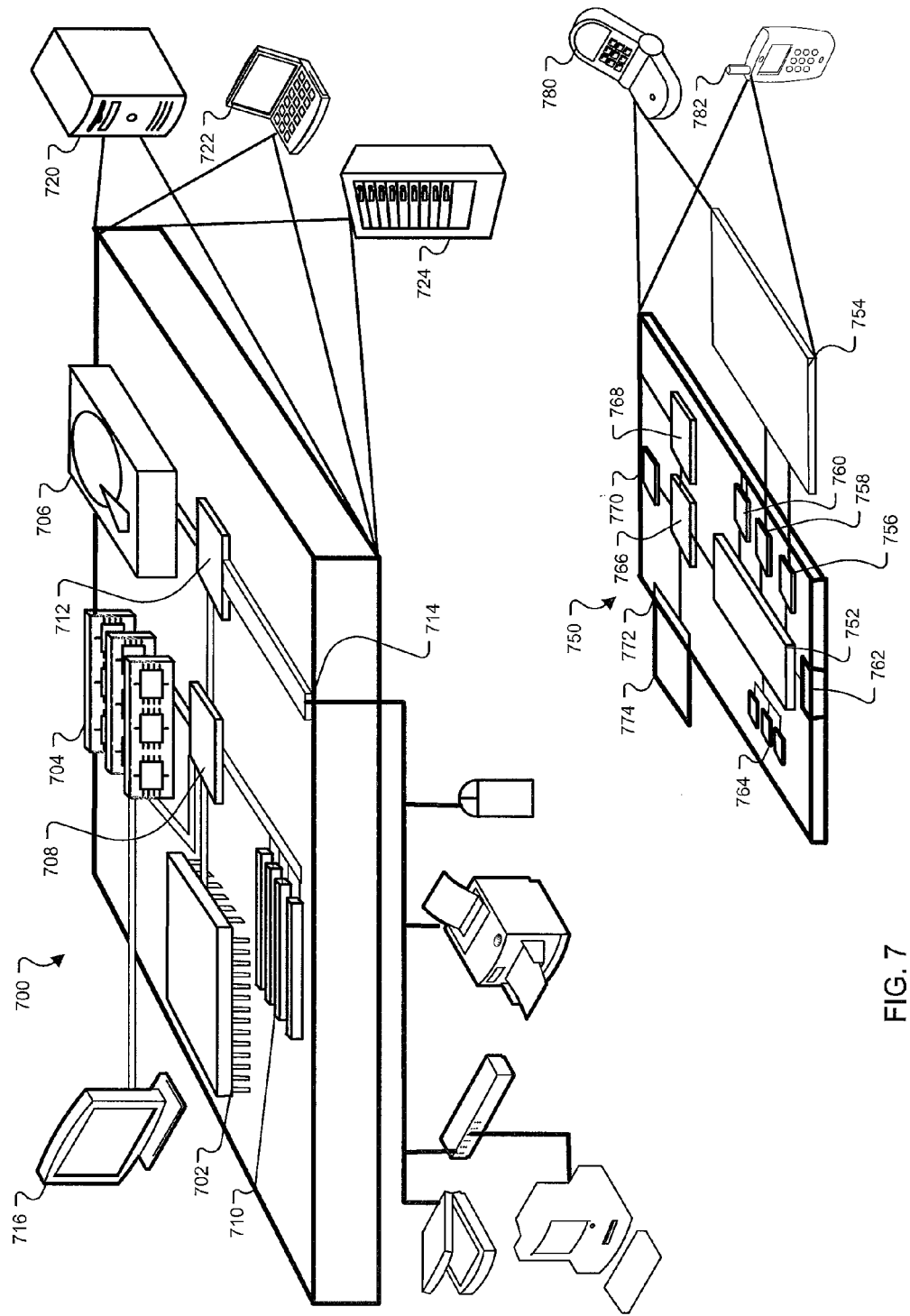
FIG. 7 shows an example of a computer device and a mobile computer device that can be used to implement the techniques described here.

FIG. 7 shows an example of a generic computer device 700 and a generic mobile computer device 750, which may be used with the techniques described here. Computing device 700 is intended to represent various forms of digital computers, such as laptops, desktops, workstations, personal digital assistants, servers, blade servers, mainframes, and other appropriate computers. Computing device 750 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 700 includes a processor 702, memory 704, a storage device 706, a high-speed interface 708 connecting to memory 704 and high-speed expansion ports 710, and a low speed interface 712 connecting to low speed bus 714 and storage device 706. Each of the components 702, 704, 706, 708, 710, and 712, are interconnected using various busses, and may be mounted on a common motherboard or in other manners as appropriate. The processor 702 can process instructions for execution within the computing device 700, including instructions stored in the memory 704 or on the storage device 706 to display graphical information for a GUI on an external input/output device, such as display 716 coupled to high speed interface 708. In other implementations, multiple processors and/or multiple buses may be used, as appropriate, along with multiple memories and types of memory. Also, multiple computing devices 700 may be connected, with each device providing portions of the necessary operations (e.g., as a server bank, a group of blade servers, or a multi-processor system).

The memory 704 stores information within the computing device 700. In one implementation, the memory 704 is a volatile memory unit or units. In another implementation, the memory 704 is a non-volatile memory unit or units. The memory 704 may also be another form of computer-readable medium, such as a magnetic or optical disk.

The storage device 706 is capable of providing mass storage for the computing device 700. In one implementation, the storage device 706 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 704, the storage device 706, memory on processor 702, or a propagated signal.

The high speed controller 708 manages bandwidth-intensive operations for the computing device 700, while the low speed controller 712 manages lower bandwidth-intensive operations. Such allocation of functions is exemplary only. In one implementation, the high-speed controller 708 is coupled to memory 704, display 716 (e.g., through a graphics processor or accelerator), and to high-speed expansion ports 710, which may accept various expansion cards (not shown). In the implementation, low-speed controller 712 is coupled to storage device 706 and low-speed expansion port 714. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 720, or multiple times in a group of such servers. It may also be implemented as part of a rack server system 724. In addition, it may be implemented in a personal computer such as a laptop computer 722. Alternatively, components from computing device 700 may be combined with other components in a mobile device (not shown), such as device 750. Each of such devices may contain one or more of computing device 700, 750, and an entire system may be made up of multiple computing devices 700, 750 communicating with each other.

Computing device 750 includes a processor 752, memory 764, an input/output device such as a display 754, a communication interface 766, and a transceiver 768, among other components. The device 750 may also be provided with a storage device, such as a microdrive or other device, to provide additional storage. Each of the components 750, 752, 764, 754, 766, and 768, are interconnected using various buses, and several of the components may be mounted on a common motherboard or in other manners as appropriate.

The processor 752 can execute instructions within the computing device 750, including instructions stored in the memory 764. The processor may be implemented as a chipset of chips that include separate and multiple analog and digital processors. The processor may provide, for example, for coordination of the other components of the device 750, such as control of user interfaces, applications run by device 750, and wireless communication by device 750.

Processor 752 may communicate with a user through control interface 758 and display interface 756 coupled to a display 754. The display 754 may be, for example, a TFT LCD (Thin-Film-Transistor Liquid Crystal Display) or an OLED (Organic Light Emitting Diode) display, or other appropriate display technology. The display interface 756 may comprise appropriate circuitry for driving the display 754 to present graphical and other information to a user. The control interface 758 may receive commands from a user and convert them for submission to the processor 752. In addition, an external interface 762 may be provide in communication with processor 752, so as to enable near area communication of device 750 with other devices. External interface 762 may provide, for example, for wired communication in some implementations, or for wireless communication in other implementations, and multiple interfaces may also be used.

The memory 764 stores information within the computing device 750. The memory 764 can be implemented as one or more of a computer-readable medium or media, a volatile memory unit or units, or a non-volatile memory unit or units. Expansion memory 774 may also be provided and connected to device 750 through expansion interface 772, which may include, for example, a SIMM (Single In Line Memory Module) card interface. Such expansion memory 774 may provide extra storage space for device 750, or may also store applications or other information for device 750. Specifically, expansion memory 774 may include instructions to carry out or supplement the processes described above, and may include secure information also. Thus, for example, expansion memory 774 may be provide as a security module for device 750, and may be programmed with instructions that permit secure use of device 750. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 764, expansion memory 774, memory on processor 752, or a propagated signal that may be received, for example, over transceiver 768 or external interface 762.

Device 750 may communicate wirelessly through communication interface 766, which may include digital signal processing circuitry where necessary. Communication interface 766 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 768. In addition, short-range communication may occur, such as using a Bluetooth, WiFi, or other such transceiver (not shown). In addition, GPS (Global Positioning System) receiver module 770 may provide additional navigation- and location-related wireless data to device 750, which may be used as appropriate by applications running on device 750.

Device 750 may also communicate audibly using audio codec 760, which may receive spoken information from a user and convert it to usable digital information. Audio codec 760 may likewise generate audible sound for a user, such as through a speaker, e.g., in a handset of device 750. Such sound may include sound from voice telephone calls, may include recorded sound (e.g., voice messages, music files, etc.) and may also include sound generated by applications operating on device 750.

The computing device 750 may be implemented in a number of different forms, as shown in the figure. For example, it may be implemented as a cellular telephone 780. It may also be implemented as part of a smartphone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to measuring motion data for particular drills, though other forms of data gathering and comparison may also be employed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented athletic performance analysis method, comprising:
   causing a transmission, to a client computing device that is remote from a server system, of code that is configured to enable the client computing device to obtain dribbling data reflecting motion of a basketball containing one or more motion sensors during one or more basketball dribbling drills performed by an athlete;
   obtaining, at the server system and from the client computing device, first dribbling data that characterizes motion of a basketball containing at least one motion sensor during performance of a first basketball dribbling drill by an athlete handling the basketball;
   obtaining, at the server system and from the client computing device, second dribbling data that characterizes motion of the basketball during performance of a second basketball dribbling drill that is different in form from the first basketball dribbling drill, and represents the athlete handling the basketball;

creating and storing action data by identifying a plurality of portions of the first dribbling data and the second dribbling data, where each of the portions correspond to one or more actions by the athlete;

comparing the action data for the athlete, with the server system, to corresponding aggregated action data for a plurality of other athletes to determine a relative skill level for the athlete with respect to the one or more actions; and storing data for a report that reflects the determined relative skill level of the athlete, wherein the first dribbling data and the second dribbling data is generated based on data captured by the at least one motion sensor in the basketball that senses motion during the first and second basketball dribbling drills, and capture of data by the at least one motion sensor and wireless transmission of the captured data from circuitry in the basketball that is connected to the motion sensor is performed in response to a request that is wirelessly transmitted to the circuitry in the basketball by the client computing device.

2. The method of claim 1, further comprising capturing the dribbling data with the at least one motion sensor.

3. The method of claim 1, further comprising determining a relative skill level for the athlete corresponding to the first basketball dribbling drill, and determining a relative skill level for the athlete corresponding to a subsequent plurality of basketball dribbling drills.

4. The method of claim 1, wherein the report includes a ranking of the athlete within a continuum of athletic performance and one or more instructions directed to reducing weaknesses identified in the athlete's performance.

5. The method of claim 1, further comprising obtaining third dribbling data reflecting motion of the basketball during one or more basketball dribbling drills performed by the athlete at a time subsequent to obtaining the first dribbling data, and performing a comparison of the first dribbling data and the third dribbling data.

6. The method of claim 1, further comprising comparing information from the first dribbling data and the second dribbling data to data representing athletic development of an aggregated plurality of athletes, to generate a predicted athletic performance trend for the athlete.

7. The method of claim 1, wherein the data for the report represents an overall skill level for the athlete, and a plurality of levels for each of a plurality of actions that were tested by the first basketball dribbling drill and the second basketball dribbling drill.

8. The method of claim 1, wherein the action data for the athlete and the aggregated action data for the plurality of other athletes is matched to common portions of common drills performed by each of the athletes.

9. The method of claim 1, wherein the first basketball dribbling drill comprises dribbling the basketball in a figure-8 pattern.

10. The method of claim 1, wherein the first basketball dribbling drill comprises dribbling the basketball a fixed number of times.

11. The method of claim 1, wherein the first basketball dribbling drill comprises dribbling the basketball one or more times before shooting the basketball.

12. A computer-implemented athletic performance analysis system, comprising:

a) a server system configured to:

cause a transmission, to a client computing device, of code that is configured to enable the client computing device to obtain dribbling data reflecting motion of a basketball containing at least one motion sensor during one or more basketball dribbling drills performed by an athlete;

obtain, from the client computing device, first dribbling data that characterizes motion of the basketball during performance of a first basketball dribbling drill by an athlete handling the basketball;

obtain, from the client computing device, second dribbling data that characterizes motion of the basketball during performance of a second basketball dribbling drill that is different in form from the first basketball dribbling drill, and represents the athlete handling the basketball;

create and storing action data identifying a plurality of portions of the first dribbling data and the second dribbling data, where each of the portions correspond to one or more actions by the athlete;

compare the action data for the athlete to corresponding aggregated action data for a plurality of other athletes to determine a relative skill level of the athlete with respect to one or more actions; and store data for a report that reflects the relative skill level of the athlete; and b) the client computing device that is remote from the server system and configured to:

receive the code that is configured to enable the client computing device to obtain dribbling data reflecting motion of the basketball during one or more basketball dribbling drills performed by the athlete;

send, to the server system, the second dribbling data; and c) the basketball containing at least one motion sensor, wherein the first dribbling data and the second dribbling data is generated based on data captured by the at least one motion sensor in the basketball that senses motion during the first and second basketball dribbling drills, and capture of data by the at least one motion sensor and wireless transmission of the captured data from circuitry in the basketball that is connected to the motion sensor is performed in response to a request that is wirelessly transmitted to the circuitry in the basketball by the client computing device.

13. The computer-implemented athletic performance analysis system of claim 12, wherein the server system is further configured to identify common features for athletes of a known skill level and to generate rules for determining how other athletes compare to the known skill level.

14. The computer-implemented athletic performance analysis system of claim 13, wherein the server system is further configured to identify common features in motion-related data from the athletes of a known skill level and to generate rules that are predictive for classifying other athletes according to the known skill level.

15. The computer-implemented athletic performance analysis system of claim 12, wherein the server system is further configured to analyze the first dribbling data from the athlete from a first time period and the second dribbling data from a second time period for the athlete, and comparing differences between the first dribbling data and the second dribbling data to trend data for the athletes of a known skill level to predict a skill level for the athlete.

16. The computer-implemented athletic performance analysis system of claim 12, wherein the client computing device includes a wireless interface configured to communicate with the basketball.

17. The computer-implemented athletic performance analysis system of claim 12, wherein the server system is further configured to correlate an identity of the client computing device with an account, and to debit an accountholder associated with the account for the report.

18. The computer-implemented athletic performance analysis system of claim 12, wherein the report includes a ranking of the athlete within a continuum of athletic performance and one or more instructions directed to reducing weaknesses identified in the athlete's performance.

19. An article comprising one or more tangible computer-readable data storage media containing program code operable to cause one or more machines to perform operations, the operations comprising:
   causing a transmission, to a client computing device that is remote from a server system, of code that is configured to enable the client computing device to obtain dribbling data reflecting motion of a basketball containing one or more motion sensors during one or more basketball dribbling drills performed by an athlete;
   obtaining, at the server system and from the client computing device, first dribbling data that characterizes motion of a basketball containing at least one motion sensor during performance of a first basketball dribbling drill by an athlete handling the basketball;
   obtaining, at the server system and from the client computing device, second dribbling data that characterizes motion of the basketball during performance of a second basketball dribbling drill that is different in form from the first basketball dribbling drill, and represents the athlete handling the basketball;
   creating and storing action data by identifying a plurality of portions of the first dribbling data and the second dribbling data, where each of the portions correspond to one or more actions by the athlete;
   comparing the action data for the athlete, with the server system, to corresponding aggregated action data for a plurality of other athletes to determine a relative skill level for the athlete with respect to the one or more actions; and
   storing data for a report that reflects the determined relative skill level of the athlete, wherein
   the first dribbling data and the second dribbling data is generated based on data captured by the at least one motion sensor in the basketball that senses motion during the first and second basketball dribbling drills, and
   capture of data by the at least one motion sensor and wireless transmission of the captured data from circuitry in the basketball that is connected to the motion sensor is performed in response to a request that is wirelessly transmitted to the circuitry in the basketball by the client computing device.

20. The article of claim 19, wherein the operations further comprise determining a relative skill level for the athlete corresponding to the first basketball dribbling drill, and determining a relative skill level for the athlete corresponding to a subsequent plurality of basketball dribbling drills.

21. The article of claim 19, wherein the report includes a ranking of the athlete within a continuum of athletic performance and one or more instructions directed to reducing weaknesses identified in the athlete's performance.

22. The article of claim 19, wherein the operations further comprise obtaining third dribbling data reflecting motion of the basketball during one or more basketball dribbling drills performed by the athlete at a time subsequent to obtaining the first dribbling data, and performing a comparison of the first dribbling data and the third dribbling data.

23. The article of claim 19, wherein the operations further comprise comparing information from the first dribbling data and the second dribbling data to data representing athletic development of an aggregated plurality of athletes, to generate a predicted athletic performance trend for the athlete.

24. A computer-implemented athletic performance analysis system, comprising:
   a) a server system configured to:
      cause a transmission, to a client computing device, of code that is configured to enable the client computing device to obtain dribbling data reflecting motion of a basketball containing at least one motion sensor during one or more basketball dribbling drills performed by an athlete;
      obtain, from the client computing device, first dribbling data that characterizes motion of the basketball during performance of a first basketball dribbling drill by an athlete handling the basketball;
      obtain, from the client computing device, second dribbling data that characterizes motion of the basketball during performance of a second basketball dribbling drill that is different in form from the first basketball dribbling drill, and represents the athlete handling the basketball;
      create and storing action data identifying a plurality of portions of the first dribbling data and the second dribbling data, where each of the portions correspond to one or more actions by the athlete; and
      store data for a report that reflects the relative skill level of the athlete; and
   b) means to compare the action data for the athlete to corresponding aggregated action data for a plurality of other athletes to determine a relative skill level of the athlete with respect to one or more actions; and
   c) the client computing device that is remote from the server system and configured to:
      receive the code that is configured to enable the client computing device to obtain dribbling data reflecting motion of the basketball during one or more basketball dribbling drills performed by the athlete;
      send, to the server system, the first dribbling data; and
      send, to the server system, the second dribbling data; and
   d) the basketball containing at least one motion sensor, wherein
      the first dribbling data and the second dribbling data is generated based on data captured by the at least one motion sensor in the basketball that senses motion during the first and second basketball dribbling drills, and
      capture of data by the at least one motion sensor and wireless transmission of the captured data from circuitry in the basketball that is connected to the motion sensor is performed in response to a request that is wirelessly transmitted to the circuitry in the basketball by the client computing device.

* * * * *